US012702310B2

(12) United States Patent
Lee et al.

(10) Patent No.: US 12,702,310 B2
(45) Date of Patent: Aug. 11, 2026

(54) DEVICE FOR PROVIDING AUGMENTED REALITY

(71) Applicant: Samsung Display Co., LTD., Yongin-si (KR)

(72) Inventors: Tae Hee Lee, Hwaseong-si (KR); Min Woo Kim, Hwaseong-si (KR); So Young Yeo, Suwon-si (KR); So Yeon Yoon, Uijeongbu-si (KR); Ok Yi Lee, Seoul (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 485 days.

(21) Appl. No.: 17/824,454

(22) Filed: May 25, 2022

(65) Prior Publication Data

US 2023/0139217 A1 May 4, 2023

(30) Foreign Application Priority Data

Nov. 1, 2021 (KR) ........................ 10-2021-0147734

(51) Int. Cl.
*A61B 5/021* (2006.01)
*A61B 5/00* (2006.01)
(Continued)

(52) U.S. Cl.
CPC ........ *A61B 5/02141* (2013.01); *A61B 5/0205* (2013.01); *A61B 5/02438* (2013.01);
(Continued)

(58) Field of Classification Search
CPC ............ G02B 27/0172; G02B 27/0176; G02B 2027/0141; G09G 3/32; G09G 2380/08; A61B 2562/0247
See application file for complete search history.

(56) References Cited

U.S. PATENT DOCUMENTS 9,049,998 B2 6/2015 Brumback et al.
10,181,507 B2 1/2019 Bower et al.
(Continued)

FOREIGN PATENT DOCUMENTS

JP 5887026 3/2016
JP 2020012970 A 1/2020
(Continued)

*Primary Examiner* — Benjamin J Klein
*Assistant Examiner* — Thien Jason Tran
(74) *Attorney, Agent, or Firm* — CANTOR COLBURN LLP

(57) ABSTRACT

A device for providing augmented reality may include a support frame supporting at least one transparent lens, an image display module displaying augmented reality content through the at least one transparent lens, a blood-pressure information detector connected to the support frame to detect at least one blood-pressure related information including a blood-pressure, a heart rate, and oxygen saturation in case that a skin of the user touches the blood-pressure information detector, a skin information detector connected to the support frame to detect at least one skin related information including a moisture level and an oil level of the user's skin in case that the user's skin touches the skin information detector, and a control module that controls the image display module to display the at least one blood-pressure related and the at least one skin related information as augmented reality contents.

20 Claims, 21 Drawing Sheets

(51) Int. Cl.

| | |
|---|---|
| ***A61B 5/0205*** | (2006.01) |
| ***A61B 5/024*** | (2006.01) |
| ***A61B 5/145*** | (2006.01) |
| ***G02B 27/01*** | (2006.01) |
| ***G09G 3/32*** | (2016.01) |

(52) U.S. Cl.

CPC .......... *A61B 5/14542* (2013.01); *A61B 5/443* (2013.01); *A61B 5/6803* (2013.01); *G02B 27/0172* (2013.01); *G02B 27/0176* (2013.01); *G09G 3/32* (2013.01); *A61B 2562/0247* (2013.01); *G02B 2027/0141* (2013.01); *G09G 2380/08* (2013.01)

(56) References Cited

U.S. PATENT DOCUMENTS

| | | | | |
|---|---|---|---|---|
| 10,568,573 | B2 * | 2/2020 | Campbell | A61B 5/0205 |
| 10,962,789 | B1 | 3/2021 | Lewis | |
| 11,443,683 | B2 | 9/2022 | Kim et al. | |
| 11,460,700 | B2 | 10/2022 | Yamamoto | |
| 11,462,595 | B2 | 10/2022 | Lee et al. | |
| 11,515,366 | B2 | 11/2022 | Hong et al. | |
| 11,985,882 | B2 | 5/2024 | Lee et al. | |
| 2012/0050044 | A1 | 3/2012 | Border et al. | |
| 2013/0044042 | A1 * | 2/2013 | Olsson | G06F 3/017 345/8 |
| 2017/0231490 | A1 * | 8/2017 | Toth | A61B 18/24 600/558 |
| 2018/0014903 | A1 * | 1/2018 | Shan | G02B 27/0172 |
| 2019/0142138 | A1 * | 5/2019 | Chen | A61K 8/988 132/200 |
| 2021/0325625 | A1 * | 10/2021 | Maric | G02B 7/02 |
| 2021/0375048 | A1 * | 12/2021 | Kang | G02B 27/0093 |

FOREIGN PATENT DOCUMENTS

| | | | |
|---|---|---|---|
| KR | 2000-0073400 | | 12/2000 |
| KR | 10-2018-0118488 | | 10/2018 |
| KR | 20190011849 | A | 2/2019 |
| KR | 20210002171 | A | 1/2021 |
| KR | 20210012181 | A | 2/2021 |
| KR | 10-2021-0051268 | | 5/2021 |
| KR | 20210065245 | A | 6/2021 |
| KR | 20210117373 | A | 9/2021 |

* cited by examiner

DEVICE FOR PROVIDING AUGMENTED REALITY

CROSS-REFERENCE TO RELATED APPLICATION(S)

This application claims priority to and benefits of Korean Patent Application No. 10-2021-0147734 under 35 U.S.C. § 119 filed on Nov. 1, 2021 in the Korean Intellectual Property Office (KIPO), the entire contents of which are incorporated herein by reference.

BACKGROUND

1. Technical Field

The disclosure relates to a device for providing augmented reality.

2. Description of Related Art

Recently, as electronic devices and display devices that implement virtual reality (VR) have been developed, interest in the VR is increasing. Technologies that may realize augmented reality (AR) and mixed reality (MR) as a next stage of the virtual reality are also being studied.

The augmented reality is a display technology in which a virtual object or an image information is displayed in a superimposed manner on an environment of a real world to further increase an effect of reality, unlike the virtual reality entirely based on a virtual world.

While the virtual reality has been limitedly applied only to fields such as games and virtual experiences, the augmented reality may be applied in various ways to the real environment. As an example, the augmented reality is attracting attention as a next-generation display technology suitable for ubiquitous environments, and internet of things (IoT) environments. This augmented reality (AR) is an example of the mixed reality in that the AR displays a mixture of the real world and additional information of the virtual world.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

A purpose of the disclosure is to provide a device to provide an augmented reality that may detect and display health-related information of a user such as a blood-pressure, a heart rate, a skin oil level, and a skin moisture level as augmented reality content.

Further, a purpose of the disclosure is to provide a device for providing augmented reality in which a micro LED display panel of a LEDoS (Light Emitting Diode on Silicon) structure is applied as each of an image display module and a light-emitting member for health information detection.

Purposes in accordance with the disclosure are not limited to the above-mentioned purposes. Other purposes and advantages in accordance with the disclosure may be understood from the following descriptions and more clearly understood from embodiments in accordance with the disclosure. Further, it will be readily appreciated that the purposes and advantages in accordance with the disclosure may be realized by features and combinations thereof as disclosed in the claims.

According to an embodiment, a device for providing augmented reality, the device may include a support frame supporting at least one transparent lens; an image display module that displays augmented reality content through the at least one transparent lens; a blood-pressure information detector connected to the support frame that detects at least one blood-pressure related information including a blood-pressure, a heart rate, and oxygen saturation of a user in case that a skin of the user touches the blood-pressure information detector; a skin information detector connected to the support frame that detects at least one skin related information including a moisture level and an oil level of the user's skin in case that the user's skin touches the skin information detector; and a control module that controls the image display module to display the at least one blood-pressure related and the at least one skin related information as augmented reality contents.

In an embodiment, the blood-pressure information detector may include a first light-emitting member that selectively emits one of first color light of a visible-light wavelength band, a second color light of a visible-light wavelength band, and a third color light of an infrared ray wavelength band; a first light-receiving sensor that detects light emitting from the first light-emitting member and reflected from the user's skin, and that outputs an optical signal corresponding to an amount of the reflected light; a first pressure sensor that senses contact with the user's skin; and a first detection processor that in case that the user's skin contact with contacts the first pressure sensor is sensed, calculates a pulse wave signal reflecting blood change according to heartbeat, based on the optical signal; and detects the blood-pressure related information based on the pulse wave signal.

In an embodiment, the blood-pressure information detector may include a first light-emission driver that transmits one of first to third drive signals to the first light-emitting member to control light-emission of the first light-emitting member in response to reception of one of first to third light-emission control signals input from the first detection processor; a first signal processor that filters and rectifies the optical signal received from the first light-receiving sensor, and outputs the filtered and rectified signal as an analog signal to the first detection processor, or converts the analog signal into a digital signal by a sampling process and outputs the digital signal to the first detection processor; and a first converter that performs digital signal processing on an electrical pressure detection signal from the first pressure sensor to convert the electrical pressure detection signal to pressure data, and transmits the pressure data to the first detection processor.

In an embodiment, the first pressure sensor, the first light-emitting member and the first light-receiving sensor may face in a frontward direction, and the first pressure sensor may be disposed around and adjacent to the first light-emitting member and the first light-receiving sensor; or the first pressure sensor, the first light-emitting member and the first light-receiving sensor may face in a frontward direction, and the first pressure sensor may be disposed on and overlap a front face of each of the first light-emitting member and the first light-receiving sensor in a plan view.

In an embodiment, the first light-emitting member may face in a frontward direction from a first housing and disposed in an inner groove of the first housing, the first pressure sensor may face in the frontward direction from a first housing and may be disposed on and overlap a front face of the first light-emitting member, the first light-receiving sensor may be fixed to the first substrate and may face in a frontward direction from the first pressure sensor, and may be disposed on and overlap a front partial area of the first pressure sensor the first pressure sensor and the first substrate each may include a first optical hole corresponding to a light-emitting face of the first light-emitting member.

In an embodiment, the first pressure sensor may include a first base substrate and a second base substrate facing toward each other; a first pressure sensor electrode disposed on the first base substrate; a second pressure sensor electrode disposed on the second base substrate; and a pressure sensing layer overlapping the first pressure sensor electrode and the second pressure sensor electrode in a plan view of the first base substrate.

In an embodiment, each of the first pressure sensor electrode and the second pressure sensor electrode may include a transparent conductive material, and the pressure sensing layer may include a transparent polymer resin.

In an embodiment, the first light-emitting member may include a circuit board including a first circuit portion, a second circuit portion, and a third circuit portion; a first light-emitting panel disposed on the first circuit portion that emits the first color light; a second light-emitting panel disposed on the second circuit portion that emits the second color light; a third light-emitting panel disposed on the third circuit portion that emits the third color light; and an optical coupler that outputs at least one of the first color light from the first light-emitting panel, the second color light from the second light-emitting panel, and the third color light from the third light-emitting panel.

In an embodiment, the first light-emitting panel may include an image display unit that emits the first color light, the second light-emitting panel may include an image display unit that emits the second color light, and the third light-emitting panel may include an image display unit that emits the third color light, and the image display unit included in each of the first light-emitting panel, the second light-emitting panel and the third light-emitting panel may include a partitioning wall disposed on a substrate and patterned in a matrix light-emitting elements respectively disposed in light-emitting areas partitioned from each other by the partitioning wall and disposed in the matrix, wherein light-emitting elements each may extend in the plan view of the substrate; a base resin disposed in the light-emitting areas that receives the light-emitting elements; and optical patterns disposed in at least one of the light-emitting areas.

In an embodiment, the circuit board may include a first connection portion disposed between the first circuit portion and the second circuit portion; and a second connection portion disposed between the second circuit portion and the third circuit portion, and the circuit board may be bent at each of the first connection portion and the second connection portion.

In an embodiment, the optical coupler may include a first reflective transmissive layer reflecting the first color light from the first light-emitting panel and transmitting the second color light and the third color light; and a second reflective transmissive layer reflecting the third light from the third light-emitting panel and transmitting the first color light and the second color light.

In an embodiment, the skin information detector may include a second light-emitting member that emits one of a first color light of a visible-light wavelength band, a second color light of a visible-light wavelength band, and a third color light of an infrared ray wavelength band; a second light-receiving sensor that detects light emitting from the second light-emitting member and reflected from the user's skin, and outputs an optical signal corresponding to an amount of the reflected light; a capacitance sensor that outputs an electrical signal based on current varied in case that a reference current amount thereof varies due to the user's skin contact; a second pressure sensor sensing the user's skin touch; and a second detection processor that in case that the user's skin touch with the second pressure sensor is sensed, the second detection processor detects a moisture level of the user's skin based on the optical signal and detects an oil level of the skin based on the electrical signal based on the varied current; and detects the skin related information including the moisture level and the oil level.

In an embodiment, the second light-emitting member may face in a frontward direction from a second housing, and may be disposed in an inner groove of the second housing, the second pressure sensor may be disposed on and overlap a front face of the second light-emitting member in the plan view, and may face in the frontward direction from the second housing, the second light-receiving sensor may be fixed to a second substrate, and may be disposed on and overlap a front partial area of the second pressure sensor in the plan view, and may face in a frontward direction from the second pressure sensor, the capacitance sensor may be fixed to the second substrate, and may be disposed on and overlap a front partial area of the second pressure sensor in the plan view, and may face in the frontward direction from the second pressure sensor, and each of the second pressure sensor and the second substrate may include a second optical hole corresponding to a light-emitting face of the second light-emitting member.

In an embodiment, the second light-emitting member may include a circuit board including a first circuit portion, a second circuit portion, and a third circuit portion; a first light-emitting panel disposed on the first circuit portion that emits the first color light; a second light-emitting panel disposed on the second circuit portion that emits the second color light; a third light-emitting panel disposed on the third circuit portion that emits the third color light; and an optical coupler that outputs at least one of the first color light from the first light-emitting panel, the second color light from the second light-emitting panel, and the third color light from the third light-emitting panel.

In an embodiment, the image display module may include an image display unit connected to a side or each of opposing sides of the support frame or integral with the support frame to display an image of augmented reality content; and an image transmission member that transmits the image to the transparent lens, and the image display module displays the image of the augmented reality content through the image transmission member and reflective members of the transparent lens by the control module.

In an embodiment, the image display unit may include a partitioning wall disposed on a substrate and patterned in a matrix; light-emitting elements respectively disposed in light-emitting areas partitioned from each other by the partitioning wall and disposed in the matrix, wherein each of the light-emitting elements may extend in a plan view of the substrate; a base resin disposed in the light-emitting areas and that receives the light-emitting elements; and optical patterns disposed in at least one of the light-emitting areas.

In an embodiment, the light-emitting areas may include a first light-emitting area, a second light-emitting area, and a third light-emitting area or a first light-emitting area, a second light-emitting area, a third light-emitting area and a fourth light-emitting area disposed in each pixel area and disposed in the matrix.

In an embodiment, the first light-emitting area may include a first light-emitting element that emits light of a first color selected from red, green, and blue; the second light-emitting area may include a second light-emitting element that emits light of a second color selected from red, green, and blue and different from the first color; the third light-emitting area may include a third light-emitting element that emits light of a third color selected from red, green, and blue and different from the first and second colors; and the fourth light-emitting area may include a fourth light-emitting element that emits light of a fourth color, the light of the fourth color and one of the first color light, the second color light and the third color light being of a same wavelength band.

In an embodiment, the first light-emitting area, the second light-emitting area, the third light-emitting area and the fourth light-emitting area may have a same size or a same planar area, and a distance between the first light-emitting area and the second light-emitting area neighboring each other in a horizontal direction or a diagonal direction, a distance between the second light-emitting area and the third light-emitting area neighboring each other in the horizontal direction or the diagonal direction, a distance between the first light-emitting area and the third light-emitting area neighboring each other in the horizontal direction or the diagonal direction, and a distance between the third light-emitting area and the fourth light-emitting area neighboring each other in the horizontal direction or the diagonal direction may be equal to each other based on a size or a planar area of each of the first light-emitting area, the second light-emitting area, the third light-emitting area and the fourth light-emitting area.

In an embodiment, at least one of the sizes or planar areas of the may be different from each other, and a distance between the first light-emitting area and the second light-emitting area neighboring each other in a horizontal direction or a diagonal direction, a distance between the second light-emitting area and the third light-emitting area neighboring each other in the horizontal direction or the diagonal direction, a distance between the first light-emitting area and the third light-emitting area neighboring each other in the horizontal direction or the diagonal direction, and a distance between the third light-emitting area and the fourth light-emitting area neighboring each other in the horizontal direction or the diagonal direction may be equal to or different from each other based on a size or a planar area of each of the first light-emitting area, the second light-emitting area, the third light-emitting area and the fourth light-emitting area.

The device for providing the augmented reality according to an embodiment displays mixture of the augmented reality content including the health-related information about the user with the real world, thereby increasing usability and user satisfaction of the device for providing the augmented reality.

The device for providing the augmented reality according to an embodiment uses the micro LED display panel as each of the image display module and the light-emitting member for detecting health information, thereby further reducing a size of the device for providing the augmented reality and improving portability thereof.

Effects according to the embodiments are not limited to those as mentioned above. Further various effects are included in the disclosure.

BRIEF DESCRIPTION OF DRAWINGS

The above and other aspects and features of the disclosure will become more apparent by describing in detail embodiments thereof with reference to the attached drawings, in which.

DETAILED DESCRIPTION OF THE EMBODIMENTS

Figure 1:
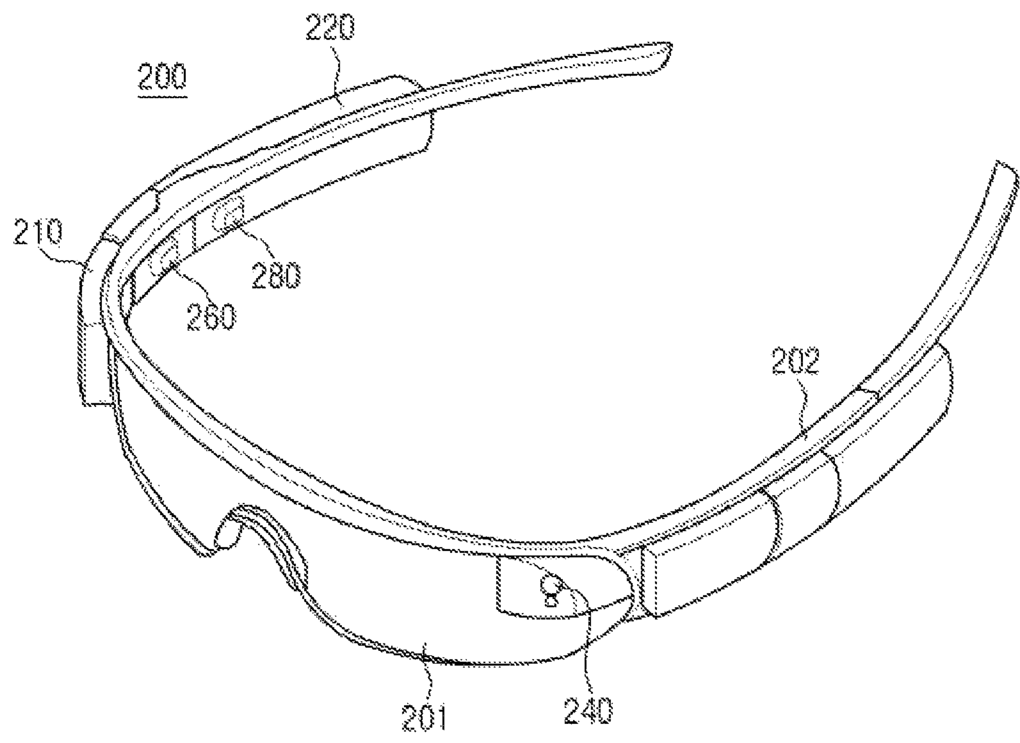
FIG. 1 is a schematic perspective view showing a device for providing augmented reality according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, sizes, thicknesses, ratios, and dimensions of the elements may be exaggerated for ease of description and for clarity. Like numbers refer to like elements throughout.

As used herein, the singular forms, "a," "an," and "the" are intended to include the plural forms as well, unless the context clearly indicates otherwise.

In the specification and the claims, the term "and/or" is intended to include any combination of the terms "and" and "or" for the purpose of its meaning and interpretation. For example, "A and/or B" may be understood to mean "A, B, or A and B." The terms "and" and "or" may be used in the conjunctive or disjunctive sense and may be understood to be equivalent to "and/or."

In the specification and the claims, the phrase "at least one of" is intended to include the meaning of "at least one selected from the group of" for the purpose of its meaning and interpretation. For example, "at least one of A and B" may be understood to mean "A, B, or A and B."

It will also be understood that when a layer is referred to as being "on" another layer or substrate, it can be directly on the other layer or substrate, or intervening layers may also be present. The same reference numbers indicate the same components throughout the specification. It will be understood that when an element (or a region, a layer, a portion, or the like) is referred to as "being on", "connected to" or "coupled to" another element in the specification, it can be directly disposed on, connected or coupled to another element mentioned above, or intervening elements may be disposed therebetween.

It will be understood that the terms "connected to" or "coupled to" may include a physical or electrical connection or coupling.

It will be understood that, although the terms "first," "second," etc. may be used herein to describe various elements, these elements should not be limited by these terms. These terms are only used to distinguish one element from another element. For instance, a first element discussed below could be termed a second element without departing from the teachings of the disclosure. Similarly, the second element could also be termed the first element. Each of the features of the various embodiments may be combined or combined with each other, in part or in whole, and other variations are possible. Each embodiment may be implemented independently of each other or may be implemented together in an association. Hereinafter, embodiments will be described in detail with reference to the accompanying drawings.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "overlap" or "overlapped" mean that a first object may be above or below or to a side of a second object, and vice versa. Additionally, the term "overlap" may include layer, stack, face or facing, extending over, covering, or partly covering or any other suitable term as would be appreciated and understood by those of ordinary skill in the art.

When an element is described as 'not overlapping' or 'to not overlap' another element, this may include that the elements are spaced apart from each other, offset from each other, or set aside from each other or any other suitable term as would be appreciated and understood by those of ordinary skill in the art.

The terms "face" and "facing" mean that a first element may directly or indirectly oppose a second element. In a case in which a third element intervenes between the first and second element, the first and second element may be understood as being indirectly opposed to one another, although still facing each other.

The terms "comprises," "comprising," "includes," and/or "including,", "has," "have," and/or "having," and variations thereof when used in this specification, specify the presence of stated features, integers, steps, operations, elements, components, and/or groups thereof, but do not preclude the presence or addition of one or more other features, integers, steps, operations, elements, components, and/or groups thereof.

The phrase "in a plan view" means viewing the object from the top, and the phrase "in a schematic cross-sectional view" means viewing a cross-section of which the object is vertically cut from the side.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, 5% of the stated value.

Unless otherwise defined or implied herein, all terms (including technical and scientific terms) used herein have the same meaning as commonly understood by one of ordinary skill in the art to which the disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a schematic perspective view showing a device for providing augmented reality according to an embodiment. Moreover, FIG. 2 is an exploded rear schematic perspective view of the device for providing the augmented reality shown in FIG. 1, and FIG. 3 is an exploded front schematic perspective view of the device for providing the augmented reality shown in FIG. 1.

Figure 2:
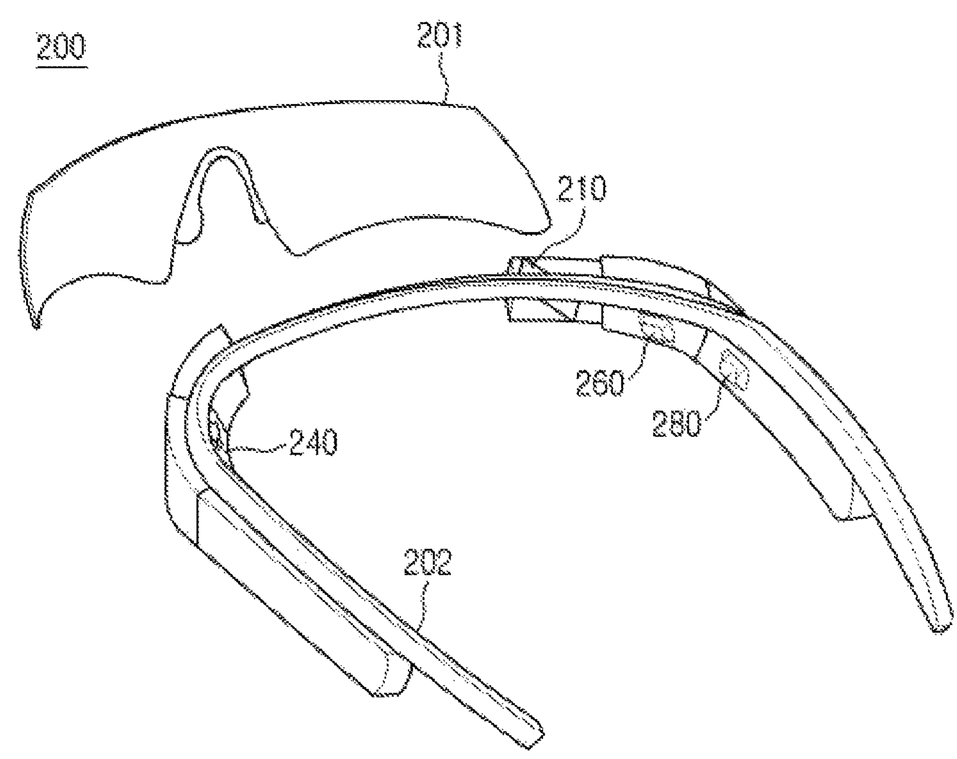
FIG. 2 is an exploded rear schematic perspective view of the device to provide the augmented reality shown in FIG. 1.
Figure 3:
FIG. 3 is an exploded front schematic perspective view of the device to provide the augmented reality shown in FIG. 1.
Figure 3:
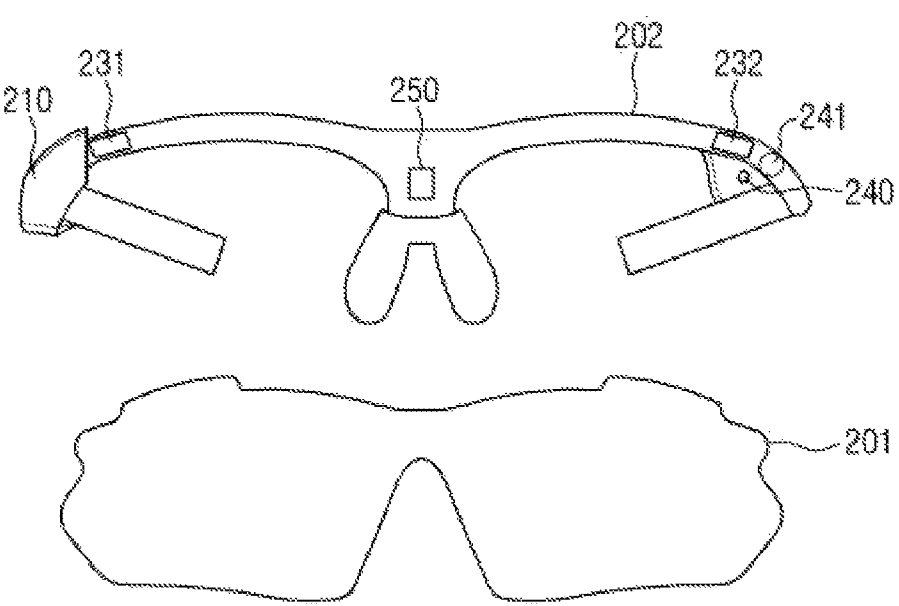

Referring to FIG. 1 to FIG. 3, a device 200 for providing augmented reality may include a support frame 202 that supports at least one transparent lens 201, at least one image display module 210, a surrounding environment detector 240, a blood-pressure information detector 260, a skin information detector 280, and a control module 220.

The support frame 202 may be formed in a spectacle shape including a spectacle frame supporting a rim of the at least one transparent lens 201 and a spectacle frame leg. A shape of the support frame 202 is not limited to the spectacle type. The support frame may be formed in a goggles type or a head mounted type including the transparent lens 201.

The transparent lens 201 may include left and right lenses integral with each other or may be composed of first and second transparent lenses as left and right lenses which are separated from each other. The transparent lens 201 which may include the left and right lenses integral with each other or may be composed of the first and second transparent lenses as left and right lenses which are separated from each other may be made of transparent or translucent glass or plastic. Thus, a user may see an image of reality through the transparent lens 201 which may include the left and right lenses integral with each other or may be composed of the first and second transparent lenses as left and right lenses which are separated from each other. The transparent lens 201, for example, each of the integrated lens or each of the first and second transparent lenses separated from each other may have refractive power in consideration of the user's eyesight.

The transparent lens 201 may further include at least one reflective member that reflects an augmented reality content image provided from the at least one image display module 210 toward the transparent lens 201 or the user's eyes, and optical members that adjust a focus and a size of the image. The at least one reflective member may be integrated with the transparent lens 201 and embedded in the transparent lens 201, and may be composed of refractive lenses having a predefined curvature or prisms.

The at least one image display module 210 may include a micro LED display device (micro-LED), a nano LED display device (nano-LED), an organic light-emitting display device (OLED), an inorganic light-emitting display device (inorganic EL), a quantum dot light-emitting display device (QED), a cathode ray display device (CRT), a liquid crystal display device (LCD), etc. Hereinafter, an example in which the micro LED display device is embodied as the image display module 210 will be described. Unless a special distinction is required, the micro LED display device applied to an embodiment will be simply abbreviated as a display device. However, an embodiment is not limited to the micro LED display device. Other display devices as listed above or otherwise are applicable herein.

The surrounding environment detector 240 is assembled to or integral with or connected to the support frame 202, and detects a distance (or a depth) thereof from an object in front of the support frame 202, illuminance, a movement direction of the support frame 202, a movement distance thereof, a tilt thereof, etc. The surrounding environment detector 240 may include a depth sensor 241 such as an infrared ray sensor or a lidar sensor, and an image sensor 250 such as a camera. Further, the surrounding environment detector 240 may further include an illuminance sensor, a human body detection sensor, and at least one motion sensor such as a gyro sensor, a tilt sensor, and an acceleration sensor. Further, the surrounding environment detector 240 may further include first and second biometric sensors 231 and 232 for detecting movement information of an eyeball or a pupil of the user.

The surrounding environment detector 240 transmits sensed signals generated from the depth sensor 241 and the at least one motion sensor to the control module 220 in real time. Moreover, the image sensor 250 transmits image data of at least one frame unit generated in real time to the control module 220. The first and second biometric sensors 231 and 232 of the surrounding environment detector 240 respectively detect pupil detection signals and transmit the same to the control module 220.

The blood-pressure information detector 260 together with the at least one image display module 210 or the control module 220 may be assembled to at least one side or a side of the support frame 202 or may be integral with the support frame 202. FIG. 1 shows an example in which one blood-pressure information detector 260 together with the control module 220 is disposed at one side or a side of the support frame 202. However, the blood-pressure information detector 260 may be formed at each of both sides and a rear face of the support frame 202. In one example, the blood-pressure information detector 260 may be formed at each of both sides of the support frame 202 and on an inner face of the support frame 202.

The blood-pressure information detector 260 may operate in a blood-pressure measurement mode in case that it is determined that the detector has touched the user's skin. Further, the blood-pressure information detector 260 may operate in the blood-pressure measurement mode under a mode control signal from the control module 220.

In case that the blood-pressure information detector 260 is set to the blood-pressure measurement mode, the blood-pressure information detector 260 may detect at least one blood-pressure related information such as a blood-pressure, a heart rate, an oxygen saturation, blood flow change, etc. In case that blood-pressure information detectors 260 are formed, blood-pressure related information values respectively detected from the blood-pressure information detectors 260 may be collected and calculated into an average value. The at least one blood-pressure related information such as the blood-pressure, the heart rate, the oxygen saturation, and the blood flow change as measured in real time is transmitted to the control module 220. Accordingly, the control module 220 may transmit the at least one blood-pressure related information detected in real time to a mobile communication device pre-paired therewith such as a smartphone or a notebook computer. The at least one blood-pressure related information detected in real time may be displayed via a preset application program on the smartphone or the laptop computer, or may be shared with a medical institution via an application program.

The skin information detector 280 together with the at least one image display module 210 or the blood-pressure information detector 260 may be assembled to at least one side or a side of the support frame 202, or may be integral with the support frame 202. The skin information detector 280 may also be formed on each of both sides and a rear face of the support frame 202.

The skin information detector 280 may operate in an oil and moisture measurement mode in case that it is determined that the skin information detector 280 has touched the skin of the user. Further, the skin information detector 280 may operate the in oil and moisture measurement mode under the mode control signal from the control module 220.

In case that the skin information detector 280 is set to the oil and moisture measurement mode, the skin information detector 280 may detect a reflective light amount from the skin and a light reflectance of the skin using a light-emitting member, a pressure sensor, a light-receiving sensor, a capacitance sensor, a second detection processor, etc. Moreover, the skin information detector 280 measures skin related information such as an oil level and a moisture level of the skin based on the reflective light amount from the skin and the light reflectance of the skin. The skin related information such as the skin moisture level and the skin oil level as measured in real time is transmitted to the control module 220. Accordingly, the control module 220 may transmit the skin related information such as the oil level and the moisture level detected in real time to the mobile communication device pre-paired therewith such as a smartphone or a notebook computer. The skin-related information detected in real time may be displayed via a preset application program on the smartphone or the laptop computer, or may be shared with a medical institution via an application program.

The control module 220 together with the at least one image display module 210 may be assembled to at least one side or a side of the support frame 202 or may be integral with the support frame 202. The control module 220 supplies augmented reality content data to the at least one image display module 210 so that the at least one image display module 210 displays the augmented reality content, for example, the augmented reality content image. At the same time, the control module 220 receives the sensed signals, the image data, and the pupil detection signals from the surrounding environment detector 240 in real time, and receives the blood-pressure related and the skin related information from the blood-pressure related and skin information detectors 260 and 280.

The control module 220 converts and rearranges the blood-pressure related and skin related information received from the blood-pressure related and skin information detectors 260 and 280 into preset graphic and text information. Moreover, the control module 220 additionally converts the text information into sound information to generate content data including the blood-pressure related and the skin related information. The control module 220 transmits the content data including the blood-pressure related and skin related information to the image display module 210 and a separate sound device, etc. such that contents including the blood-pressure related and the skin related information are displayed as augmented reality content information. Further, the control module 220 may transmit the blood-pressure related information and skin related information as real-time detected to the mobile communication device pre-paired therewith such as a smartphone or a laptop computer. The control module 220 may further include a short-range wireless communication module such as a Wi-Fi or Bluetooth module or a long-range wireless communication module such as a 4G, 5G, or LTE module.

Figure 4:
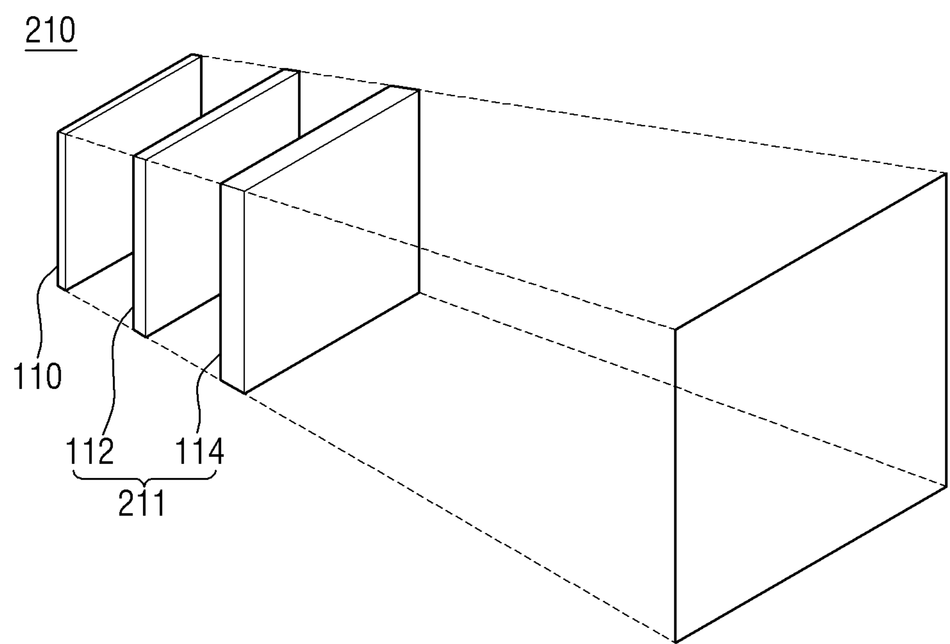
FIG. 4 is an exploded schematic perspective view schematically showing an image display module shown in FIG. 1 to FIG. 3.

FIG. 4 is an exploded schematic perspective view schematically showing the image display module shown in FIG. 1 to FIG. 3.

Referring to FIG. 4, the at least one image display module 210 that displays the augmented reality content image may be assembled to one side or a side or each of both sides of the support frame 202 or may be integral with the support frame 202.

The image display module 210 allows the augmented reality content image to be displayed on the at least one transparent lens 201 so that the augmented reality content image is displayed in a superimposed manner on a reality image visible to the user through the at least one transparent lens 201. The at least one image display module 210 may include at least one image display unit 110 for displaying the augmented reality content image, and an image transmission member 211 for transmitting the augmented reality content image to the at least one transparent lens 201. The image transmission member 211 may include at least one optical member of an optical waveguide (for example, a prism), a diffusing lens 112, and a focusing lens 114. Accordingly, the augmented reality content image displayed through each image display unit 110 may be provided to the user's eyes and the at least one transparent lens 201 through the optical waveguide, the diffusion lens 112, and the at least one focusing lens 114.

The image display unit 110 included in the image display module 210 may include the micro LED display device (micro-LED), the nano LED display device (nano-LED), the organic light-emitting display device (OLED), the inorganic light-emitting display device (inorganic EL), the quantum dot light-emitting display device (QED), etc. In following descriptions, an example in which the image display unit 110 is embodied as the micro LED display device is described. However, an embodiment is not limited to the micro LED display device. Other display devices as listed above or otherwise are applicable herein.

Figure 5:
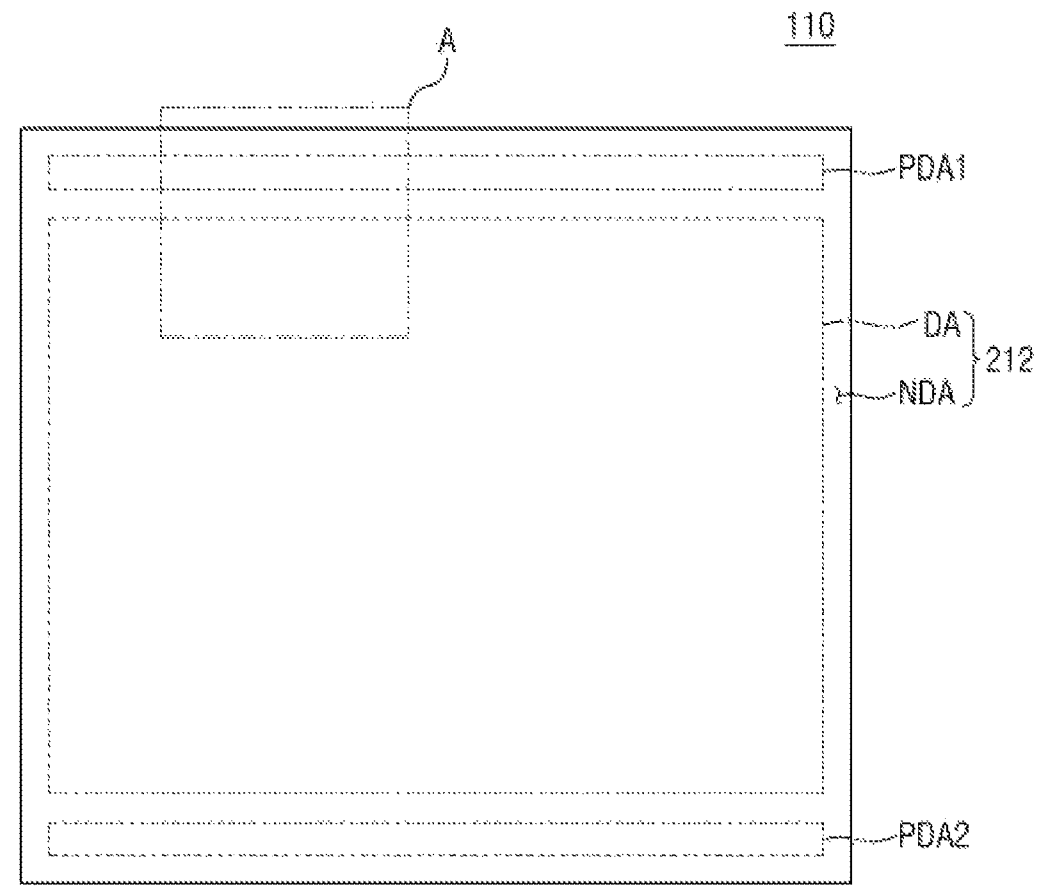
FIG. 5 is a layout diagram showing an image display unit shown in FIG. 4 in detail.
Figure 5:
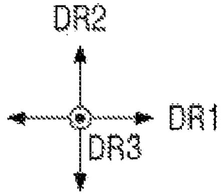

FIG. 5 is a layout diagram showing the image display unit shown in FIG. 4 in detail. Moreover, FIG. 6 is a layout diagram showing an area A of FIG. 5 in detail, and FIG. 7 is a layout diagram showing pixels shown in an area B of FIG. 6 in detail.

Figure 6:
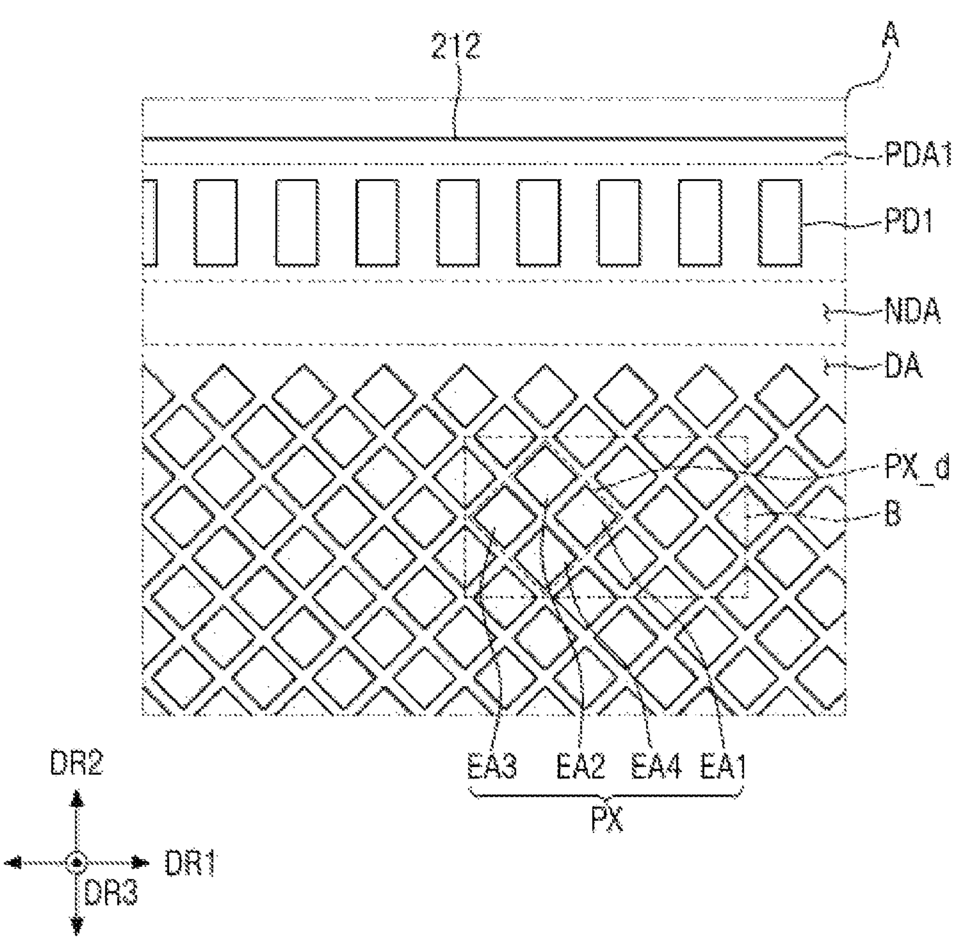
FIG. 6 is a layout diagram showing an area A of FIG. 5 in detail.
Figure 7:
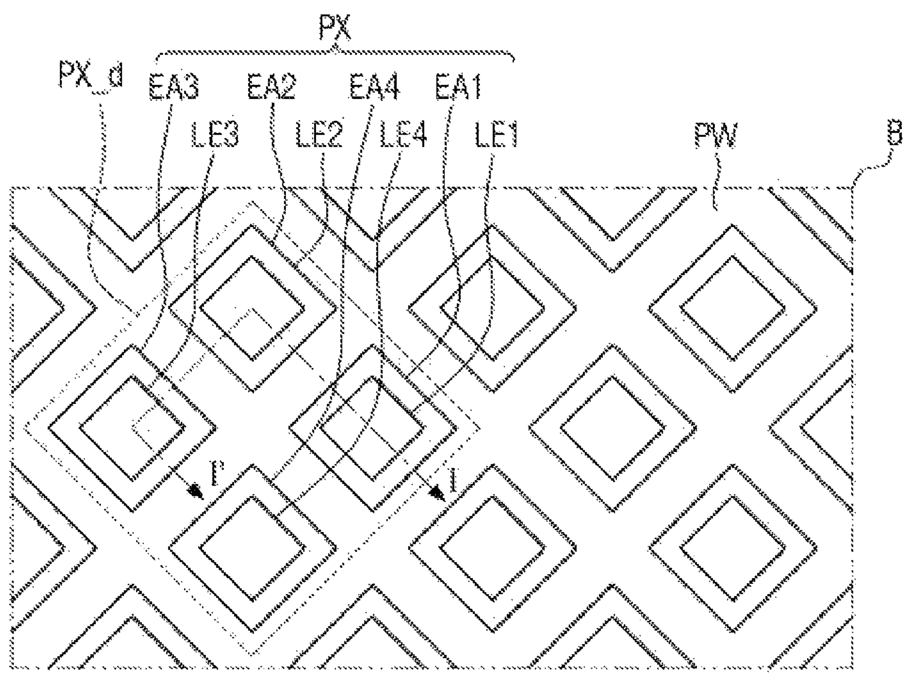
FIG. 7 is a layout diagram showing pixels shown in an area B of FIG. 6 in detail.
Figure 7:
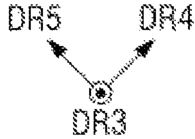

The image display unit 110 in an embodiment according to FIG. 5 to FIG. 7 is an example of an LEDoS (Light Emitting Diode on Silicon) structure in which light-emitting diode elements are disposed on a semiconductor circuit board formed using a semiconductor process. However, it should be noted that an embodiment is not limited thereto. Further, an example in which the image display unit 110 according to an embodiment is embodied as an ultra-small light-emitting diode display module (micro or nano light-emitting diode display module) including an ultra-small light-emitting diode (micro or nano light-emitting diode) as a light-emitting element has been described. However, an embodiment is not limited thereto.

Referring to FIG. 5 to FIG. 7, a first direction DR1 indicates a horizontal direction of the image display unit 110, a second direction DR2 indicates a vertical direction of the image display unit 110, and a third direction DR3 indicates a thickness direction of the display panel 212 or a thickness direction of a semiconductor circuit board 215. A fourth direction DR4 indicates a diagonal direction of the display panel 212, and a fifth direction DR5 indicates a diagonal direction intersecting the fourth direction DR4. “Left”, “right”, “upper”, and “lower” indicate a direction of the display panel 212 in a plan view. For example, “right side” indicates one side or a side in the first direction DR1, “left side” indicates the other side in the first direction DR1, “upper side” indicates one side or a side in the second direction DR2, and “lower side” indicates the other side in the second direction DR2. Further, “top” refers to one side or a side in the third direction DR3, and “bottom” refers to the other side in the third direction DR3. At least FIGS. 12 and 13 include a sixth direction DR6.

Referring to FIGS. 5 to 7, the image display unit 110 has a display panel 212 including a display area DA and a non-display area NDA.

The display panel 212 of the image display unit 110 may have a rectangular planar shape having a long-side extending in the first direction DR1 and a short-side extending in the second direction DR2. However, a planar shape of the display panel 212 is not limited thereto, and may have a polygonal shape other than the rectangular shape, a circular, oval, or irregular shape.

The display area DA may be an area in which an image is displayed, and the non-display area NDA may be an area in which an image is not displayed. A planar shape of the display area DA may be identical with the planar shape of the display panel 212. FIG. 5 illustrates that the planar shape of the display area DA is a rectangle. The display area DA may be disposed in an inner area of the display panel 212. The non-display area NDA may be disposed around the display area DA. The non-display area NDA may be disposed to surround or may be adjacent to the display area DA.

A first pad area PDA1 may be disposed in a non-display area NDA. The first pad area PDA1 may be disposed in an upper area of the display panel 212. The first pad area PDA1 may include first pads PD1 connected to an external circuit board. In one example, a second pad area PDA2 may be disposed in the non-display area NDA. The second pad area PDA2 may be disposed in a lower area of the display panel 212. The second pad area PDA2 may include second pads to be connected to the external circuit board. The second pad area PDA2 may be omitted.

The display area DA of the display panel 212 may include pixels PX. Each pixel PX may be defined as a minimum light-emitting unit that displays white light in each defined pixel area PX_d.

The pixel PX acting as the minimum unit light-emitting that displays white light in each pixel area PX_d may include light-emitting areas EA1, EA2, EA3, and EA4. In an embodiment, it is described that each pixel PX may include four light-emitting areas EA1, EA2, EA3, and EA4 arranged or disposed in a PENTILE™ matrix structure. However, the disclosure is not limited thereto. For example, each of the pixels PX may include only three light-emitting areas EA1, EA2, and EA3.

The light-emitting areas EA1, EA2, EA3, and EA4 in each pixel area PX_d may be partitioned from each other via a partitioning wall (or bank) PW. The partitioning wall PW may be disposed to surround each of first to fourth light-emitting elements LE1 to LE4 disposed in the light-emitting areas EA1, EA2, EA3, and EA4, respectively. The partitioning wall PW may be spaced apart from each of the first to fourth light-emitting elements LE1 to LE4. The partitioning wall PW may have a planar shape such as a mesh shape, or a grid shape.

FIGS. 6 and 7 illustrate that each of the light-emitting areas EA1, EA2, EA3, and EA4 defined by the partitioning wall PW has a rhombus-shaped planar shape constituting a PENTILE™ matrix structure. An embodiment of the disclosure is not limited thereto. For example, each of the light-emitting areas EA1, EA2, EA3, and EA4 defined by the partitioning wall PW may have a polygonal shape such as a square or a triangle other than a rhombus, or a circle, an oval, or an irregular shape.

Referring to FIG. 7, the first light-emitting area EA1 among the light-emitting areas EA1, EA2, EA3, and EA4 may include a first light-emitting element LE1 that emits first color light. The second light-emitting area EA2 may include a second light-emitting element LE2 emitting second color light. The third light-emitting area EA3 may include a third light-emitting element LE4 emitting third color light. The fourth light-emitting area EA4 may include a fourth light-emitting element LE4 emitting fourth color light. The first color light may be light of a wavelength band that renders one of red, green, and blue. Moreover, the second color light may be light of a wavelength band that renders one color different from the first color among red, green, and blue. On the other hand, the third color light may be light of a wavelength band that renders one color different from the first and second colors among red, green, and blue. Moreover, the fourth color light may be light of the same wavelength band as that of one of the first to third light.

Although it has been described that each of the first to fourth light-emitting elements LE1 to LE4 respectively included in the first to fourth light-emitting areas EA1 to EA4 arranged or disposed in a PENTILE™ matrix structure has a planar shape of a rhombus. Examples of the disclosure are not limited thereto. For example, each of the first to fourth light-emitting elements LE1 to LE4 may be formed in a polygonal shape such as a triangle or a quadrangle other than the rhombus shape or in a circular, oval, or irregular shape.

Each of the first light-emitting areas EA1 refers to an area emitting the first light. Each of the first light-emitting areas EA1 outputs the first light emitting from the first light-emitting element LE1. As described above, the first light may be light of a wavelength band which renders one of red, green, and blue. In one example, the first light may be light of a red wavelength band. The red wavelength band may be in a range of about 600 nm to about 750 nm, but embodiments are not limited thereto.

Each of the second light-emitting areas EA2 refers to an area emitting the second light. Each of the second light-emitting area EA2 outputs the second light emitting from the second light-emitting element LE2. The second light may be light of a wavelength band that renders one color different from the first color among red, blue, and green. In one example, the second light may be light of a blue wavelength band. The blue wavelength band may be in a range of about 370 nm to about 460 nm, but embodiments are not limited thereto.

Each of the third light-emitting areas EA3 refers to an area emitting the third light. Each of the third light-emitting areas EA3 outputs the third light emitting from the third light-emitting element LE3. The third light may be light of a wavelength band that renders one color different from the first and second colors among red, blue, and green. In one example, the third light may be light of a green wavelength band. The green wavelength band may be in a range of about 480 nm to about 560 nm, but embodiments are not limited thereto.

Each of the fourth light-emitting areas EA4 refers to an area emitting the fourth light. Each of the fourth light-emitting areas EA4 outputs the fourth light emitting from the fourth light-emitting element LE4. The fourth light may be light of a wavelength band that renders the same color as a color of one of the first to third light. In one example, the fourth light may be light of the same blue wavelength band as that of the second light, or may be light of the same green wavelength band as that of the third light. Examples of the disclosure are not limited thereto.

The second light-emitting area EA2 in each pixel PX may be alternately arranged or disposed with the fourth light-emitting area EA4 of another pixel PX adjacent thereto along the first direction DR1 as a horizontal or row direction. Moreover, the first light-emitting area EA1 and the third light-emitting area EA3 in each pixel PX may be alternately arranged or disposed with each other along the first direction DR1 as a horizontal or row direction. On the other hand, the fourth light-emitting area EA4 in each pixel PX may be alternately arranged or disposed with the second light-emitting area EA2 in another pixel PX adjacent thereto along the first direction DR1 as a horizontal or row direction.

The first light-emitting area EA1 and the fourth light-emitting area EA4 are alternately arranged or disposed with each other in the fourth direction DR4 as the first diagonal direction. The second light-emitting area EA2 and the third light-emitting area EA3 are also alternately arranged or disposed with each other in the fourth direction DR4 as the first diagonal direction. Accordingly, the second light-emitting area EA2 and the first light-emitting area EA1 are alternately arranged or disposed with each other in the fifth direction DR5 as the second diagonal direction intersecting the first diagonal direction. The third light-emitting area EA3 and the fourth light-emitting area EA4 are also alternately arranged or disposed with each other in the fifth direction DR5 as the second diagonal direction. Thus, the pixel PXs may also be arranged or disposed in a PENTILE™ matrix structure.

Sizes or planar areas of the first to fourth light-emitting areas EA1 to EA4 of each pixel PX may be the same as or different from each other. Similarly, sizes or planar areas of the first to fourth light-emitting elements LE1 to LE4 respectively formed in the first to fourth light-emitting areas EA1 to EA4 may be the same as or different from each other.

For example, an area of the first light-emitting area EA1, an area of the second light-emitting area EA2, an area of the third light-emitting area EA3, and an area of the fourth light-emitting area EA4 may be substantially equal to each other. However, an embodiment is not limited thereto. For example, the sizes of the first and second light-emitting areas EA1 and EA2 may be different from each other, the sizes of the second and third light-emitting areas EA2 and EA3 may be also different from each other, and the sizes of the third and fourth light-emitting areas EA3 and EA4 may also be different from each other. Sizes of each of at least two pairs of light-emitting areas among the first to fourth light-emitting areas EA1 to EA4 may be equal to each other.

A distance between the first and second light-emitting areas EA1 and EA2 neighboring to each other in the horizontal or diagonal direction, a distance between the second and third light-emitting areas EA2 and EA3 neighboring to each other in the horizontal or diagonal direction, a distance between the third and fourth light-emitting areas EA3 and EA4 neighboring to each other in the horizontal or diagonal direction, and a distance between the first and fourth light-emitting areas EA1 and EA4 neighboring to each other in the horizontal or diagonal direction may be equal to each other or may be different from each other as the sizes thereof are different from each other. Examples of the disclosure are not limited thereto.

The disclosure is not limited to an example in which the first light-emitting area EA1 emits the first light, the second light-emitting area EA2 emits the second light, the third light-emitting area EA3 emits the third light, and the fourth light-emitting area EA4 emits the same light as one of the first to third light. At least one light-emitting area of the first to fourth light-emitting areas EA1 to EA4 may emit fifth light. The fifth light may be light of a yellow wavelength band. For example, a main peak wavelength of the fifth light may be in a range of about 550 nm to about 600 nm, but the disclosure is not limited thereto.

Figure 8:
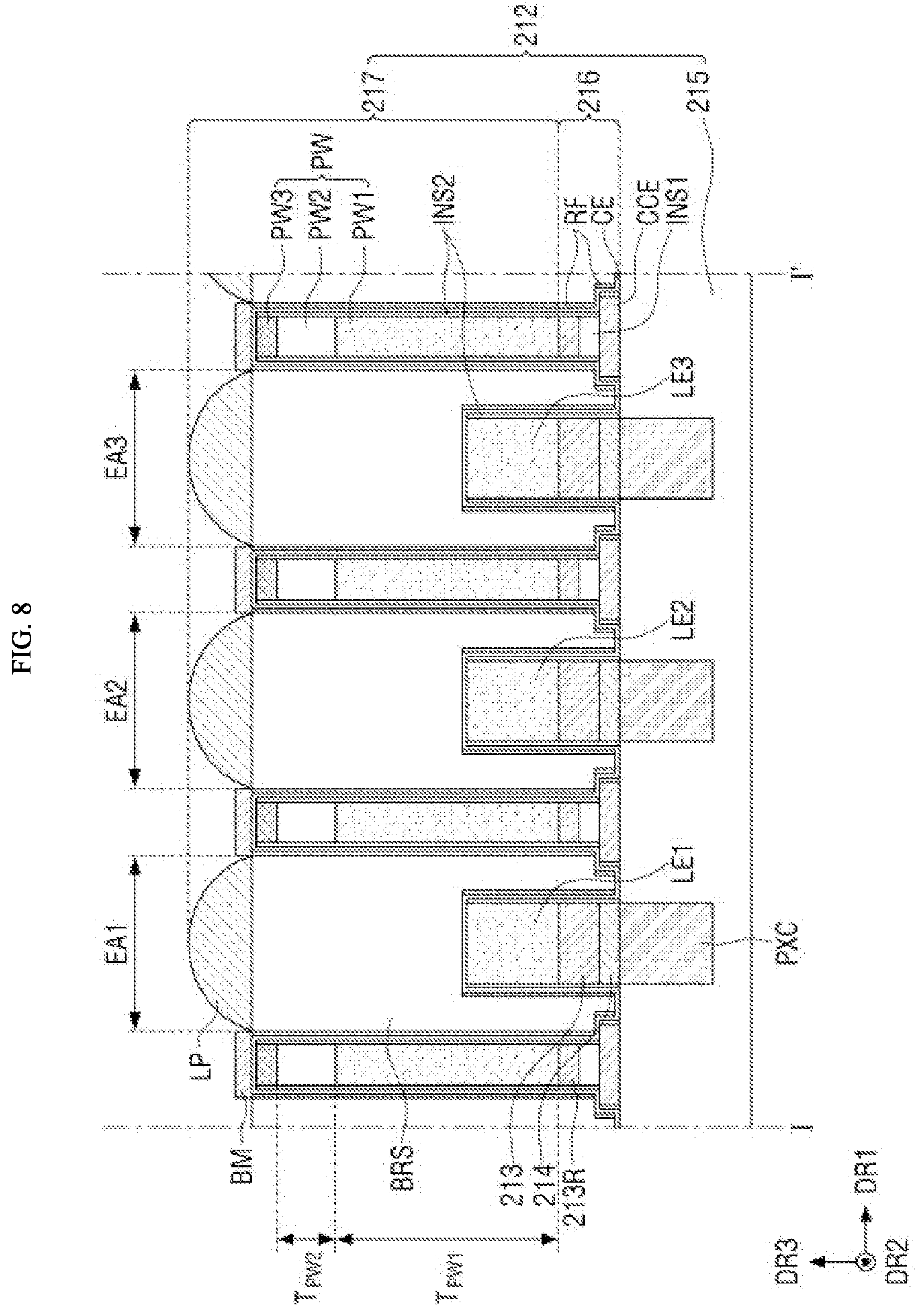
FIG. 8 is a schematic cross-sectional view showing an example of an image display unit as cut along line I-I' in FIG. 7.

FIG. 8 is a schematic cross-sectional view showing an example of an image display unit cut along line I-I' in FIG. 7. Moreover, FIG. 9 is an enlarged schematic cross-sectional view showing an example of the light-emitting element of FIG. 8 in detail.

Figure 9:
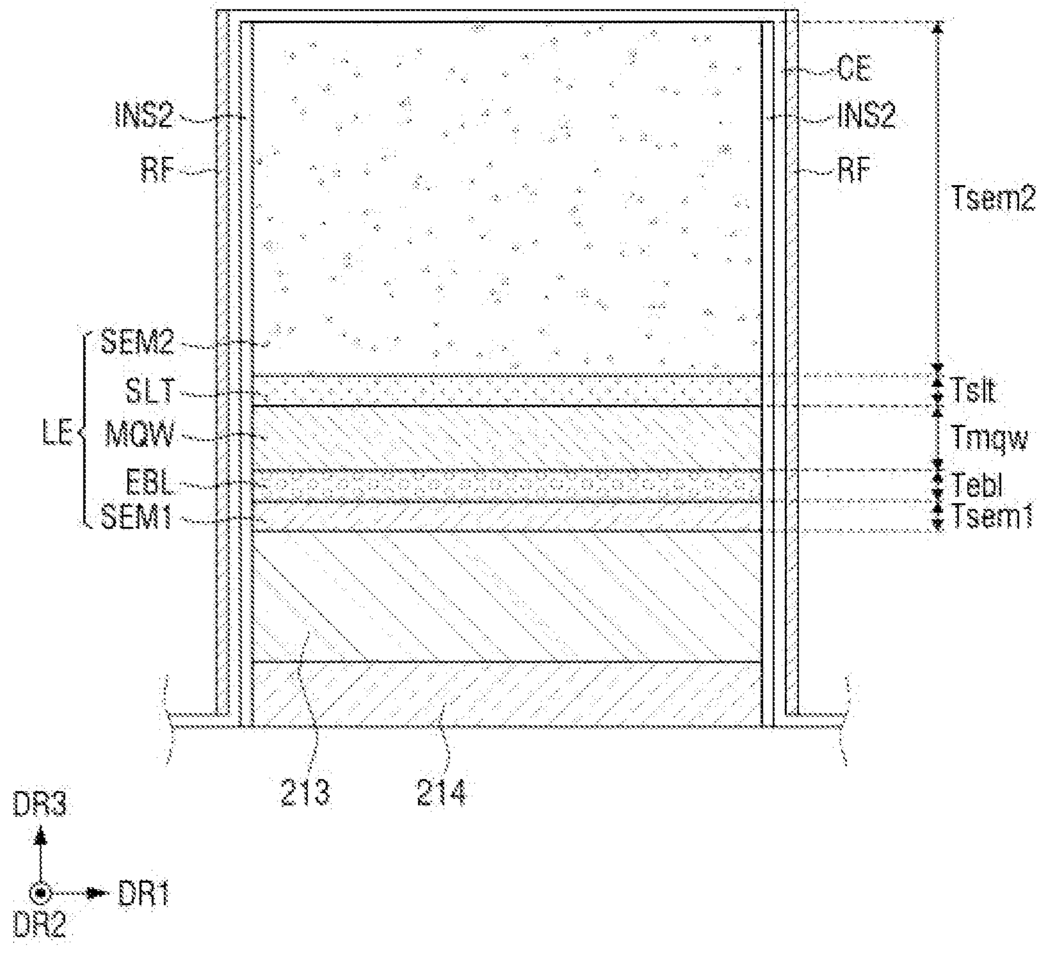
FIG. 9 is an enlarged schematic cross-sectional view showing an example of a light-emitting element of FIG. 8 in detail.

Referring to FIG. 8 and FIG. 9, the display panel 212 may include the semiconductor circuit board 215, a conductive connection layer 216, and a light-emitting element layer 217.

The semiconductor circuit board 215 may include pixel circuits PXC and pixel electrodes 214. The conductive connection layer 216 may include connection electrodes 213, the first pads PD1, a common connection electrode CCE, a first insulating layer INS1, and a conductive pattern 213R.

The semiconductor circuit board 215 may be embodied as a silicon wafer substrate formed using a semiconductor process. The pixel circuits PXC of the semiconductor circuit board 215 may be formed using a semiconductor process.

The pixel circuits PXC may be disposed in the display area (DA of FIG. 6). Each of the pixel circuits PXC may be connected to a corresponding pixel electrode 214. For example, the pixel circuits PXC and the pixel electrodes 214 may be respectively connected to each other in a one-to-one corresponding manner. Each of the pixel circuits PXC may overlap each of the light-emitting elements LE1 to LE4 in the third direction DR3. Various other modified circuit structures such as a 3T1C structure, a 2T1C structure, a 7T1C structure, and a 6T1C structure may be applied to each of the pixel circuits PXC.

Each of the pixel electrodes 214 may be disposed on a corresponding pixel circuit PXC. Each of the pixel electrodes 214 may be an exposed electrode on the pixel circuit PXC. For example, each of the pixel electrodes 214 may protrude from a top face of the pixel circuit PXC. Each of the pixel electrodes 214 may be integral with the pixel circuit PXC. Each of the pixel electrodes 214 may receive a pixel voltage or an anode voltage from the pixel circuit PXC. The pixel electrodes 214 may be made of aluminum (Al).

Each of the connection electrodes 213 may be disposed on each pixel electrode 214 corresponding thereto. Each of the connection electrodes 213 may be disposed on the pixel electrode 214. Each of the connection electrodes 213 may include a metal material for bonding each of the pixel electrodes 214 and each of the light-emitting elements LE1 to LE4 to each other.

The common connection electrode CCE may be spaced apart from the pixel electrode 214 and the connection electrode 213. The common connection electrode CCE may be disposed to surround the pixel electrode 214 and the connection electrode 213. The common connection electrode CCE may be connected to one of the first pads PD1 in the first pad area PDA1 of the non-display area NDA and receive a common voltage therefrom. The common connection electrode CCE may include a same material or a similar material as that of each of the connection electrodes 213.

A first insulating layer INS1 may be disposed on the common connection electrode CCE. A width of the first insulating layer INS1 in the first direction DR1 or the second direction DR2 may be smaller than a width of the common connection electrode CCE in the first direction DR1 or the second direction DR2. Thus, a portion of a top face of the common connection electrode CCE may be exposed while not being covered with or overlapped by the first insulating layer INS1. The exposed portion of the top face of the common connection electrode CCE that is not covered with or overlapped by the first insulating layer INS1 may contact a common electrode CE. Therefore, the common electrode CE may be connected to the common connection electrode CCE.

A conductive pattern 213R may be disposed on the first insulating layer INS1. The conductive pattern 213R may be disposed between the first insulating layer INS1 and a partitioning wall PW. A width of the conductive pattern 213R may be substantially the same as the width of the first insulating layer INS1 or a width of the partitioning wall PW. The conductive pattern 213R may be made of a residue formed by the same process in which the connection electrodes 213 and the common connection electrode CCE are formed.

The light-emitting element layer 217 may include each of the light-emitting elements LE1, LE2, LE3, and LE4, the partitioning wall PW, a second insulating layer INS2, the common electrode CE, a reflective layer RF, a light-blocking member BM, and optical patterns LP.

The light-emitting element layer 217 may include the first to fourth light-emitting areas EA1 to EA4 partitioned from each other via the partitioning wall PW. Each light-emitting element LE and at least one component of the optical pattern LP may be disposed in each of the first to fourth light-emitting areas EA1 to EA4.

Each of the light-emitting elements LE1, LE2, and LE3 of FIG. 8 may be disposed on the connection electrode 213 and in each of the light-emitting areas EA1 to EA3. A length (or a vertical dimension) in the third direction DR3 of each of the light-emitting elements LE1, LE2, and LE3 may be larger than a length in the horizontal direction thereof. The length in the horizontal direction indicates a length in the first direction DR1 or a length in the second direction DR2. For example, the length in the third direction DR3 of the first light-emitting element LE1 may be in a range of about 1 μm to about 5 μm.

Referring to FIG. 9, each of the light-emitting elements LE1, LE2, LE3, and LE4 may include a first semiconductor layer SEM1, an electron blocking layer EBL, an active layer MQW, a superlattice layer SLT, and a second semiconductor layer SEM2. The first semiconductor layer SEM1, the electron blocking layer EBL, the active layer MQW, the superlattice layer SLT, and the second semiconductor layer SEM2 may be sequentially stacked each other in the third direction DR3. In FIG. 9, the second semiconductor SEM2 layer may have a thickness Tsem2, the superlattice layer SLT may have a thickness Tslt, the active layer MQW may have a thickness Tmqw, the electron blocking layer EBL may have a thickness Tebl, and the first semiconductor SEM1 layer may have a thickness Tsem1.

The first semiconductor layer SEM1 may be disposed on the connection electrode 213. The first semiconductor layer SEM1 may be embodied as a semiconductor layer doped with first conductivity type dopant such as Mg, Zn, Ca, Se, or Ba. For example, the first semiconductor layer SEM1 may be made of p-GaN doped with p-type Mg. A thickness of the first semiconductor layer SEM1 may be in a range of about 30 to about 200 nm.

The electron blocking layer EBL may be disposed on the first semiconductor layer SEM1. The electron blocking layer EBL may act as a layer to inhibit or prevent excessive electrons from flowing into the active layer MQW. For example, the electron blocking layer EBL may be made of p-AlGaN doped with p-type Mg. A thickness of the electron blocking layer EBL may be in a range of about 10 to about 50 nm. The electron blocking layer EBL may be omitted.

The active layer MQW may be divided into first to third active layers. Each of the first to third active layers may include a material of a single or multiple quantum well structure. In case that each of the first to third active layers may include a material of the multi-quantum well structure, the structure may refer to a structure in which well layers and barrier layers may be alternately stacked each other. The first active layer may include InGaN or GaAs, and each of the second active layer and the third active layer may include InGaN. However, the disclosure is not limited thereto. The first active layer may emit light via combination between electrons and holes due to an electrical signal applied thereto. The first active layer may emit first light having a main peak wavelength in a range of about 600 nm to about 750 nm, for example, light of a red wavelength band. The second active layer may emit light via combination between electrons and holes due to an electrical signal applied thereto. The second active layer may emit third light, for example, light of a green wavelength band having a main peak wavelength in a range of about 480 nm to about 560 nm. The third active layer may emit light via combination between electrons and holes due to an electrical signal applied thereto. The third active layer may emit second light having a main peak wavelength in a range of about 370 nm to about 460 nm, for example, light of a blue wavelength band.

Each of the first to third active layers may emit light of a color varying based on a content of indium therein. For example, as the content of indium decreases, a wavelength band of the light emitting from each of the first to third active layers shifts to the red wavelength band. As the content of indium increases, the wavelength band of the light emitting from each of the first to third active layers shifts to the blue wavelength band. The content of indium (In) of the first active layer may be higher than the content of indium (In) of the second active layer. The content of indium (In) of the second active layer may be higher than the content of the indium (In) in the third active layer. For example, the content of indium (In) of the third active layer may be about 15%, the content of indium (In) of the second active layer may be about 25%, and the content of indium (In) of the first active layer may be about 35% or higher.

Each of the first to third active layers may emit light of a color varying based on the content of indium therein. Thus, the light-emitting element layer 217 of each of the light-emitting elements LE1, LE2, and LE3 may emit light of a color varying depending on the content of the indium therein, for example, may emit the first light, the second light, or the third light depending on the content of the indium therein. For example, in case that the content of indium (In) in each of the first to third active layers of the first light-emitting element LE1 is within 15%, the first light-emitting element LE1 may emit the first light in a red wavelength band having a main peak wavelength in a range of about 600 nm to about 750 nm. Moreover, in case that the content of indium (In) in each of the first to third active layers of the second light-emitting element LE2 is about 25%, the second light-emitting element LE2 may emit the second light of the green wavelength band having a main peak wavelength in a range of about 480 nm to 560 nm. Further, in case that the content of indium (In) in each of the first to third active layers of the third light-emitting element LE3 is higher than or equal to about 35%, the third light-emitting element LE3 may emit the third light of the blue wavelength band having a main peak wavelength in a range of about 370 nm to about 460 nm. Adjusting and setting the content of indium (In) in each of the first to third active layers of the fourth light-emitting element LE4 may allow the fourth light-emitting element LE4 to emit one of the first to third light, or fourth light different therefrom.

The superlattice layer SLT may be disposed on the active layer MQW. The superlattice layer SLT may act as a layer to relieve stress between the second semiconductor layer SEM2 and the active layer MQW. For example, the superlattice layer SLT may be made of InGaN or GaN. A thickness of the superlattice layer SLT may be in a range of about 50 to about 200 nm. The superlattice layer SLT may be omitted.

The second semiconductor layer SEM2 may be disposed on the superlattice layer SLT. The second semiconductor layer SEM2 may be doped with second conductivity type dopant such as Si, Ge, Sn, or the like within the spirit and the scope of the disclosure. For example, the second semiconductor layer SEM2 may be made of n-GaN doped with n-type Si. A thickness of the second semiconductor layer SEM2 may be in a range of about 2 to about 4 μm.

The partitioning wall PW may be spaced apart from each of the light-emitting elements LE1 to LE4 disposed in each of the first to fourth light-emitting areas EA1 to EA4. The partitioning wall PW may be disposed to surround each of the light-emitting elements LE1 to LE4 disposed in each of the first to fourth light-emitting areas EA1 to EA4.

The partitioning wall PW may be disposed on the common electrode connection electrodes CCE. A width of the partitioning wall PW in each of the first direction DR1 and the second direction DR2 may be smaller than a width of the common connection electrode CCE in each of the first direction DR1 and the second direction DR2. The partitioning wall PW may be spaced away from the light-emitting elements LE.

The partitioning wall PW may include a first partitioning wall PW1, a second partitioning wall PW2, and a third partitioning wall PW3. The first partitioning wall PW1 may have a thickness of $T_{PW1}$ and the second partitioning wall PW2 may have a thickness of $T_{PW2}$. The first partitioning wall PW1 may be disposed on the first insulating layer INS1. Since the first partitioning wall PW1 is formed by the same process in which the light-emitting element LE is formed, at least a partial area of the first partitioning wall PW1 may include a same material or a same material as that of the light-emitting element LE.

The second insulating layer INS2 may be disposed on side faces of the common connection electrode CCE, side faces of the partitioning wall PW, side faces of each of the pixel electrodes 214, side faces of each of the connection electrodes 213, and side faces of each of the light-emitting elements LE1 to LE4. The second insulating layer INS2 may be composed of an inorganic layer such as a silicon oxide ($SiO_2$) layer. A thickness of the second insulating layer INS2 may be in a range of approximately 0.1 μm.

The common electrode CE may be disposed on a top face and side faces of each of the light-emitting elements LE1 to LE4, and on a top face and side faces of the partitioning wall PW. For example, the common electrode CE may be disposed to cover or overlap the top face and the side faces of each of the light-emitting elements LE1 to LE4, and the top face and the side faces of the partitioning wall PW.

The common electrode CE may contact the second insulating layer INS2 disposed on the side faces of the common connection electrode CCE, the side faces of the partitioning wall PW, the side faces of each of the pixel electrodes 214, the side faces of each of the connection electrodes 213, and the side faces of each of the light-emitting elements LE1 to LE4. Further, the common electrode CE may contact a top face of the common connection electrode CCE, a top face of each of the light-emitting elements LE1 to LE4, and a top face of the partitioning wall PW.

The common electrode CE may be in contact with an exposed portion of the top face of the common connection electrode CCE not covered with or overlapped by the second insulating layer INS2 and with the top face of each of the light-emitting elements LE1 to LE4. Therefore, a common voltage supplied to the common connection electrode CCE may be applied to the light-emitting elements LE1 to LE4. For example, one end or an end of each of the light-emitting elements LE1 to LE4 may receive the pixel voltage or the anode voltage of the pixel electrode 214 via the connection electrode 213, and the other end or another end thereof may receive the common voltage via the common electrode CE. The light-emitting element LE may emit light at predefined luminance based on a voltage difference between the pixel voltage and the common voltage.

The reflective layer RF may be disposed on side faces of the common connection electrode CCE, side faces of the partitioning wall PW, side faces of each of the pixel electrodes 214, side faces of each of the connection electrodes 213, and side faces of each of the light-emitting elements LE1 to LE4. The reflective layer RF plays a role of reflecting light beams traveling not upwardly but downwardly, and in left and right directions among light beams emitting from the light-emitting elements LE1 to LE4. The reflective layer RF may include a highly reflective metal material such as aluminum (Al). A thickness of the reflective layer RF may be in a range of approximately 0.1 μm.

A base resin BRS may be disposed on a protective layer and in each of the light-emitting elements LE1 to LE4. The base resin BRS may include a transmissive organic material. The base resin BRS may further include scattering means for scattering light from the light-emitting elements LE1 to LE4 in a random direction. The scattering means may include metal oxide particles or organic particles.

A light-blocking member BM may be disposed on the partitioning wall PW. The light-blocking member BM may include a light-blocking material. The light-blocking member BM may be disposed between adjacent ones of the light-emitting areas EA1, EA2, EA3, and EA4, so that light beams of different colors of different wavelength bands from the light-emitting elements LE1 to LE4 of the light-emitting areas EA1, EA2, EA3, and EA4, respectively may be prevented from being mixed with each other. Further, the light-blocking member BM absorbs at least a portion of external light incident from an outside toward the light-emitting element layer 217 to reduce external light reflection. The light-blocking member BM may be located or disposed on the partitioning wall PW, and may further extend beyond each of the light-emitting areas EA1, EA2, EA3, and EA4. For example, a width of the light-blocking member BM may be larger than a width of the partitioning wall PW.

Each of the optical patterns LP may be selectively disposed on each of the light-emitting areas EA1, EA2, EA3, and EA4. Each of the optical patterns LP may be disposed directly on the base resin BRS of each of the light-emitting areas EA1, EA2, EA3, and EA4. The optical pattern LP may have a shape protruding upwardly (for example, in a direction from each of the light-emitting elements LE1 to LE4 toward each optical pattern LP). For example, a cross-sectional shape of each optical pattern LP may include an upwardly convex lens shape. Each optical pattern LP may be disposed on the underlying base resin BRS, and the underlying light-blocking member BM. A width of each optical pattern LP may be equal to, larger than, or smaller than a width of each of the light-emitting areas EA1, EA2, EA3, and EA4. Each optical pattern LP may collect each of the first to third light or the fourth light emitting from each of the light-emitting areas EA1, EA2, EA3, and EA4 and passing through the base resin BRS.

Figure 10:
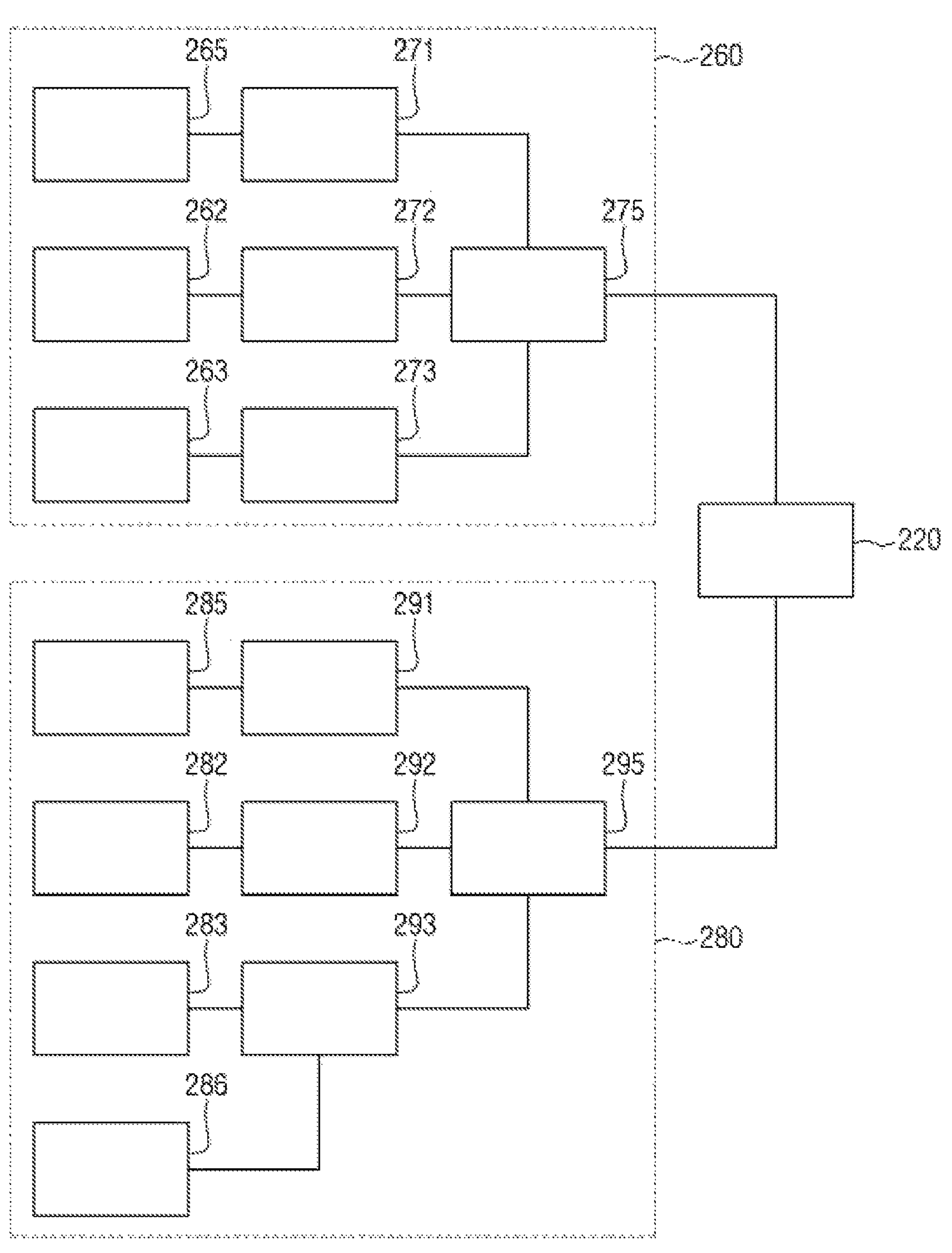
FIG. 10 is a block diagram showing a configuration of each of a blood-pressure information detector and a skin information detector as shown in FIG. 1 and FIG. 2.

FIG. 10 is a block diagram showing a configuration of each of blood-pressure and skin information detectors shown in FIG. 1 and FIG. 2 in detail.

The blood-pressure information detector 260 shown in FIG. 10 may include a first light-emitting member 262, a first pressure sensor 263, a first light-receiving sensor 265, a first signal processor 271, a first light-emission driver 272, a first converter 273, and a first detection processor 275.

The first light-emitting member 262 may emit light of one color of the first color of a visible-light wavelength band, the second color of a visible-light wavelength band, or the third color of an infrared ray wavelength band in response to reception of one of first to third drive signals from the first light-emission driver 272. In one example, the first light-emitting member 262 may emit red light of a visible-light wavelength band, green light of a visible-light wavelength band, and light of an infrared ray band in response to reception of the first to third drive signals, respectively.

The first light-emission driver 272 transmits one of the first to third drive signals in response to reception one of first to third light-emission control signals of the first detection processor 275 to the first light-emitting member 262. The first light-emission driver 272 may modulate a pulse width of one of the first to third drive signals based on a duty ratio included in one of the first to third light-emission control signals and may transmit the drive signal having the modulated pulse width to the first light-emitting member 262.

The first light-receiving sensor 265 may face in the same direction (for example, in a frontward direction) as a direction in which the first light-emitting member 262 may face. Accordingly, the first light-receiving sensor 265 detects amount of light emitting from the first light-emitting member 262 and reflected from a skin or an object in front thereof. Moreover, the first light-receiving sensor 265 transmits an optical signal corresponding to the reflected light amount to the first signal processor 271. The first light-receiving sensor 265 may include a photodiode or a phototransistor. In one example, the first light-receiving sensor 265 may be embodied as a CMOS image sensor or a CCD sensor that senses light. A light-emitting structure of the first light-emitting member 262 and a light-receiving structure of the first light-receiving sensor 265 will be described later in more detail with reference to the accompanying drawings.

The first signal processor 271 may filter and rectify an optical signal received from the first light-receiving sensor 265 and output the filtered and rectified signal as an analog signal. The first signal processor 271 may convert the analog signal into a digital signal using an analog signal sampling process and output the digital signal.

The first pressure sensor 263 may face in the same direction (for example, in a frontward direction) as a direction in which the first light-emitting member 262 and the first light-receiving sensor 265 may face. The first pressure sensor 263 may be disposed at a periphery adjacent to the first light-emitting member 262 and the first light-receiving sensor 265, or may overlap or be stacked on a front face of each of the first light-emitting member 262 and the first light-receiving sensor 265.

The first pressure sensor 263 detects a touch pressure onto the user's skin or the object, and transmits an electrical pressure detection signal corresponding to the touch pressure to the first converter 273.

The first converter 273 may perform digital signal processing on the electrical pressure detection signal from the first pressure sensor 263 to convert the detection signal into pressure data, and transmit the pressure data to the first detection processor 275.

The first detection processor 275 selects one of the first to third light-emission control signals and outputs the selected on to the first light-emission driver 272 to control the first light-emitting member 262 to emit light of one of the first color of the visible-light wavelength band, the second color of the visible-light wavelength band, or the third color of the infrared ray wavelength band. The light-emission control signal may include a duty ratio that controls a light-emitting period. The first detection processor 275 may alternately select and output the first to third light-emission control signals.

For example, green color light or red color light of the visible-light wavelength band invade into an artery and is readily absorbed therein. Thus, a peak value of a waveform detected in case that measuring the blood-pressure may be accurately detected. Therefore, in case that measuring information such as the blood-pressure, the heart rate, or the skin aging of the user, the first detection processor 275 transmits the first or second light-emission control signal to the first light-emission driver 272 to control the first light-emitting member 262 to emit green or red color light in the visible-light wavelength band. On the contrary, light in the infrared ray wavelength band penetrates into a blood vessel and is readily absorbed therein. Thus, a waveform continuously detected during blood-pressure measurement may be accurately analyzed. Accordingly, the first detection processor 275 transmits the third light-emission control signal to the first light-emission driver 272 in case that the detector detects a blood flow amount, blood oxygen saturation, a hemoglobin content, etc. of the user to control the first light-emitting member 262 to emit light in the infrared ray wavelength band.

In case that the first detection processor 275 calculates a value of the pressure applied to the first pressure sensor 263 based on the pressure data, the first detection processor 275 calculates a pulse wave signal that is related to blood change according to heartbeat, based on the optical signal input through the first signal processor 271. Moreover, the first detection processor 275 measures and generates at least one blood-pressure related information among the blood-pressure, the heart rate, the blood flow, and the blood oxygen saturation of the user based on the pulse wave signal. The at least one blood-pressure related information is transmitted to the control module 220. The control module 220 controls the image display module 210 to display contents including the blood-pressure related information as augmented reality content information. A method for measuring and generating the blood-pressure related information by the first detection processor 275 will be described later in conjunction with the accompanying drawings.

The skin information detector 280 shown in FIG. 10 include a second light-emitting member 282, a second pressure sensor 283, a second light-receiving sensor 285, a capacitance sensor 286, a second signal processor 291, a second light-emission driver 292, a second converter 293, and a second detection processor 295.

The second light-emitting member 282 emits one of light of the first color of the visible-light wavelength band, light of the second color of the visible-light wavelength band or light of the third color of the infrared ray wavelength band in response to reception one drive signal of first to third drive signals from the second light-emission driver 292.

The second light-emission driver 292 transmits one of first to third drive signals to the second light-emitting member 282 in response to reception of one of first to third light-emission control signals of the second detection processor 295.

The second light-receiving sensor 285 and the second light-emitting member 282 may face in the same direction. Thus, the second light-receiving sensor 285 may sense light emitting from the second light-emitting member 282 and reflected from the skin or the object in front thereof. Moreover, the second light-receiving sensor 285 transmits an optical signal corresponding to an amount of the light reflected from the skin or the object in front thereof to the second signal processor 291. The second light-receiving sensor 285 may be embodied a CMOS image sensor or a CCD sensor that senses light.

The second signal processor 291 may filter and rectify the optical signal received from the second light-receiving sensor 285 and thus convert the filtered and rectified signal into an analog signal, and transmit the converted analog signal to the second detection processor 295. Further, the second signal processor 291 may sample the filtered and rectified optical signal, convert the sampled signal into a digital signal, and transmit the digital to the second detection processor 295.

The second pressure sensor 283 may face in the same direction as a direction in which the second light-emitting member 282 and the second light-receiving sensor 285 face. The second pressure sensor 283 may be disposed in one periphery adjacent to the second light-emitting member 282 and the second light-receiving sensor 285. By way of example, the second pressure sensor 283 may be disposed on a front face of each of the second light-emitting member 282 and the second light-receiving sensor 285 so as to overlap each of the second light-emitting member 282 and the second light-receiving sensor 285.

The second pressure sensor 283 detects a touch pressure against the user's skin or an object, and transmits a pressure detection signal according to the touch pressure to the second converter 293.

The capacitance sensor 286 is disposed to be in contact with the user's skin or the object, and detects a change in a current amount due to contact thereof with the user's skin or the object. A current having a preset reference current amount flows through the capacitance sensor 286. In case that the user's skin or the object comes into contact therewith, the current amount varies based on an amount of oil on a surface of the user's skin or the object. Accordingly, in case that the current amount varies due to the contact of the sensor 286 with the user's skin or the object, the capacitance sensor 286 transmits the varied current amount to the second converter 293 or the second detection processor 295.

The second converter 293 may perform digital signal processing on an electrical pressure detection signal from the second pressure sensor 283 to convert the same into pressure data, and transmit the pressure data to the second detection processor 295. Further, the second converter 293 may generate a current amount change signal or data according to the current amount of the electrical signal input from the capacitance sensor 286 and transmit the generated signal or data to the second detection processor 295.

The second detection processor 295 selects one light-emission control signal from among from the first to third light-emission control signals and outputs the selected one to the second light-emission driver 292 to control the second light-emitting member 282 to emit light of one color of the first color of the visible-light wavelength band, the second color of the visible-light wavelength band, or the third color of the infrared ray wavelength band.

The second detection processor 295 calculates a magnitude of the pressure applied to the second pressure sensor 283 based on the pressure data, and calculates a reflected light signal based on an optical signal input through the second signal processor 291. Moreover, the second detection processor 295 detects moisture level information of the user's skin using the reflected light signal. Further, the second detection processor 295 detects skin oil level information based on the current change signal or data of the capacitance sensor 286. The skin related information including the moisture level and the oil level is transmitted to the control module 220. The control module 220 controls the image display module 210 to display contents including the skin related information as augmented reality content information. A method for measuring and generating the skin related information by the second detection processor 295 will be described later in conjunction with the accompanying drawings.

Figure 11:
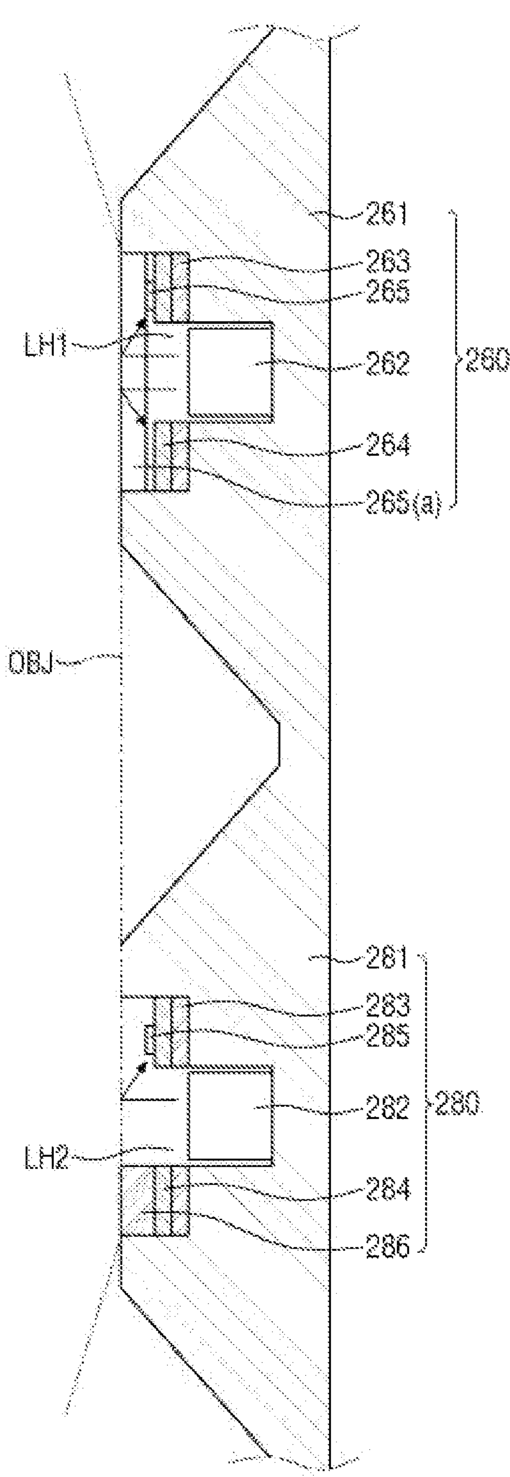
FIG. 11 is a schematic cross-sectional view showing an arrangement structure of a light-emitting member, a pressure sensor, and a light-receiving sensor of each of the blood-pressure and skin information detectors shown in FIGS. 1 and 2.

FIG. 11 is a schematic cross-sectional view showing an arrangement structure of the light-emitting member, the pressure sensor, and the light-receiving sensor of each of the blood-pressure and skin information detectors shown in FIGS. 1 and 2.

Referring to FIG. 11, the first light-emitting member 262 of the blood-pressure information detector 260 may face in a frontward direction from the first housing 261 and may be seated in an inner groove of the first housing 261.

The first pressure sensor 263 may face in the frontward direction from the first housing 261 and be disposed on a front face of the first light-emitting member 262 in an overlapping manner therewith. A rear face of the first pressure sensor 263 may be attached to a front face of the first housing 261 via an adhesive member or the like within the spirit and the scope of the disclosure. The first pressure sensor 263 may include a first optical hole LH1 corresponding to a light-emitting face of the first light-emitting member 262 so that light emitting from the first light-emitting member 262 may emit in a frontward direction (an arrow direction). The first optical hole LH1 may be an optical hole through which light may pass, or may be a physically formed hole passing through the first pressure sensor 263. By way of example, the first optical hole LH1 may include a mixture of a physical hole and an optical hole.

The first light-receiving sensor 265 may be fixed to the first substrate 264 and disposed on a front partial area of the first pressure sensor 263 in an overlapping manner therewith and may face in a frontward direction from the first pressure sensor 263. A rear face of the first substrate 264 may be attached to a front face of the first pressure sensor 263 via an adhesive member or the like within the spirit and the scope of the disclosure. The first substrate 264 may include the first optical hole LH1 corresponding to the light-emitting face of the first light-emitting member 262 so that light emitting from the first light-emitting member 262 may emit in the frontward direction (arrow direction). A window 265(*a*) for protecting the first light-receiving sensor 265 and the first substrate 264 may be disposed on a front face of each of the first light-receiving sensor 265 and the first substrate 264.

The first light-emitting member 262 may emit light of each of red in the visible-light wavelength band, green in the visible-light wavelength band, and infrared ray light in the frontward direction (arrow direction) in response to reception of each of the first to third drive signals from the first light-emission driver 272. Accordingly, the first light-receiving sensor 265 may detect reflected light emitting from the first light-emitting member 262 and reflected from the skin or the object OBJ in front thereof through the window 265*a*.

The second light-emitting member 282 of the skin information detector 280 may be seated in an inner groove of the second housing 281 and may face in a frontward direction from the second housing 281.

The second pressure sensor 283 may be disposed on a front face of the second light-emitting member 282 in an overlapping manner therewith and may face in a frontward direction from the second housing 281. A rear face of the second pressure sensor 283 may be attached to a front face of the second housing 281 via an adhesive member or the like within the spirit and the scope of the disclosure. The second pressure sensor 283 may include a second optical hole LH2 corresponding to a light-emitting face of the second light-emitting member 282 so that light emitting from the second light-emitting member 282 may emit in the frontward direction (arrow direction). The second optical hole LH2 may be an optical hole through which light may pass, or may be a physically formed hole passing through the second pressure sensor 283. By way of example, the second optical hole LH2 may include a mixture of a physical hole and an optical hole.

The second light-receiving sensor 285 may be fixed to the second substrate 284 and disposed on a front partial area of the second pressure sensor 283 in an overlapping manner therewith and may face in a frontward direction from the second pressure sensor 283. A rear face of the second substrate 284 may be attached to a front face of the second pressure sensor 283 via an adhesive member or the like within the spirit and the scope of the disclosure.

The capacitance sensor 286 together with the second light-receiving sensor 285 may be fixed to the second substrate 284. The capacitance sensor 286 may face in a frontward direction from the second pressure sensor 283. The capacitance sensor 286 may also be disposed on the second substrate 284 so as to overlap a front partial area of the second pressure sensor 283 and may face in the frontward direction from the second pressure sensor 283. In case that a reference current amount that flows by itself varies due to contact of the capacitance sensor 286 with the user's skin or the object, the capacitance sensor 286 transmits the varied current amount to the second converter 293 or the second detection processor 295, or the like within the spirit and the scope of the disclosure.

The second light-emitting member 282 may emit light of each of red in the visible-light wavelength band, green in the visible-light wavelength band, and infrared ray light in the frontward direction (arrow direction) in response to reception of each of the first to third drive signals from the second light-emission driver 292. Accordingly, the second light-receiving sensor 285 may detect reflected light emitting from the second light-emitting member 282 and reflected from the skin or the object OBJ in front thereof.

Figure 12:
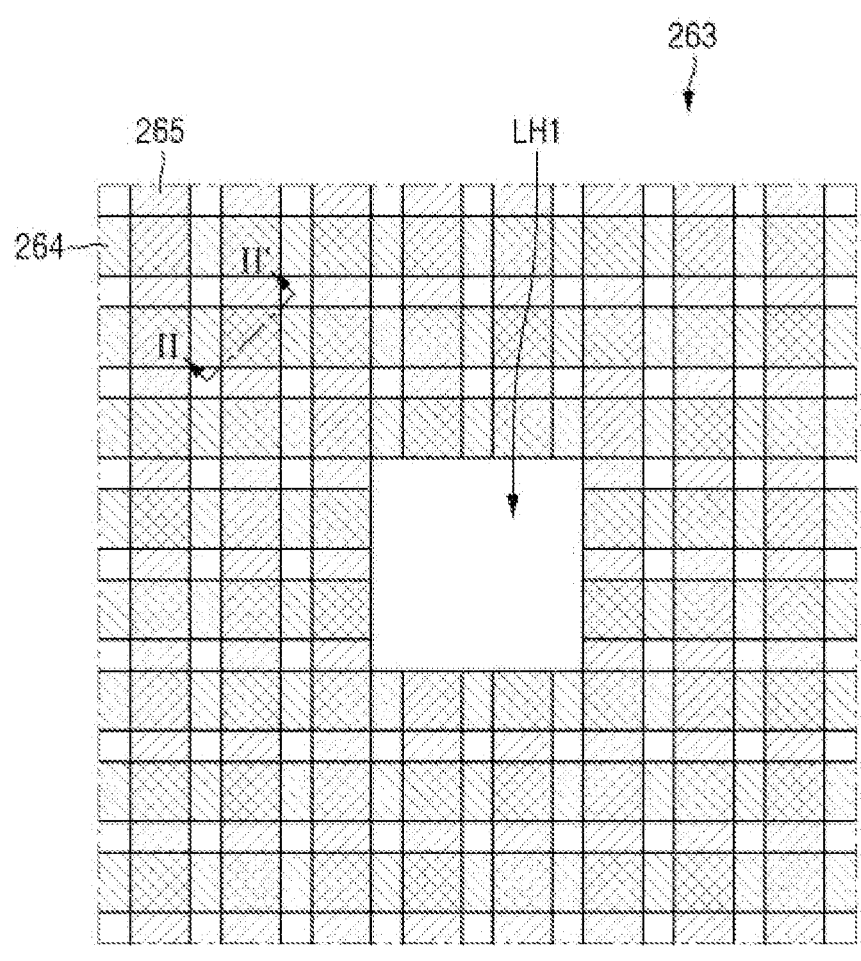
FIG. 12 is a layout diagram showing pressure sensor electrodes and an optical hole of the pressure sensor shown in FIG. 11.
Figure 12:
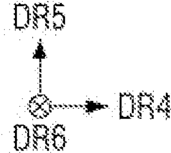
Figure 13:
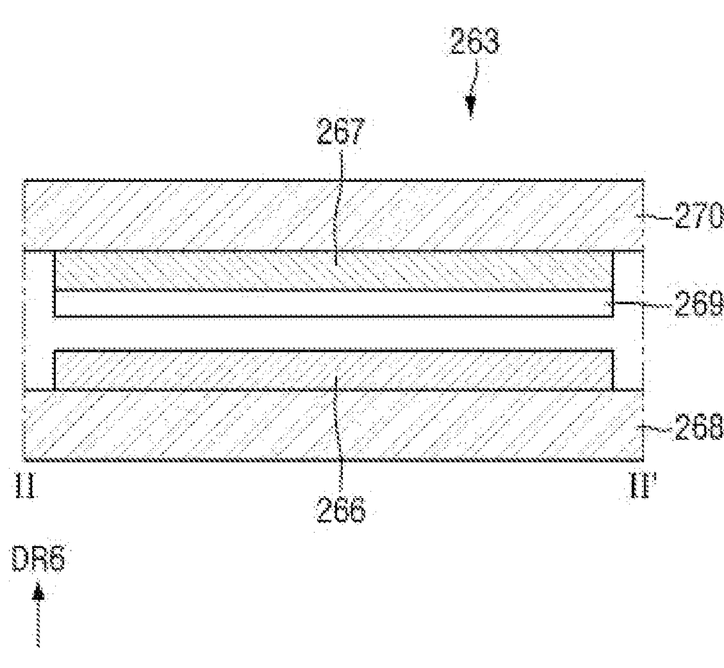
FIG. 13 is a schematic cross-sectional view showing an example of the pressure sensor of FIG. 11.

FIG. 12 is a layout diagram showing the pressure sensor electrodes and the optical hole of the pressure sensor shown in FIG. 11. FIG. 13 is a schematic cross-sectional view showing an example of the pressure sensor of FIG. 11. FIG. 13 shows an example of a cross-sectional structure of the first pressure sensor 263 cut along II-II' of FIG. 12.

Referring to FIG. 12 and FIG. 13, the first pressure sensor 263 may include a first base substrate 268, a first pressure sensor electrode 266, a second base substrate 270, a second pressure sensor electrode 267, and a pressure sensing layer 269 disposed between the first pressure sensor electrode 266 and the second pressure sensor electrode 267. Although not shown in the drawings, a structure of the second pressure sensor 283 may also be the same as that of the first pressure sensor 263. Thus, description of the structure of the second pressure sensor 283 is replaced with description of that of the first pressure sensor 263.

Each of the first and second base substrates 268 and 270 of the first pressure sensor 263 may be embodied as a polyethylene terephthalate (PET) layer, or a polyimide layer.

The first pressure sensor electrodes 266 may be disposed on one face or a face of the first base substrate 268 facing toward the second base substrate 270. The second pressure sensor electrodes 267 may be disposed on one face or a face of the second base substrate 270 facing toward the first base substrate 268. Each of the first pressure sensor electrode 266 and the second pressure sensor electrode 267 may include a conductive metal or material such as silver (Ag), copper (Cu), and ITO. One of the first pressure sensor electrode 266 and the second pressure sensor electrode 267 may act as a pressure driving electrode, and the other may act as a pressure sensing electrode.

The pressure sensing layer 269 may be disposed between the first and second pressure sensor electrodes 266 and 267. The pressure sensing layer 269 may contact at least one of the first and second pressure sensor electrodes 266 and 267. For example, the pressure sensing layer 269 may be in contact with the second pressure sensor electrode 267 as shown in FIG. 13. By way of example, the pressure sensing layer 269 may be in contact with the first pressure sensor electrode 266. The pressure sensing layer 269 may include a pressure-sensitive material. The pressure-sensitive material may include carbon or nanoparticles made of a metal such as nickel, aluminum, tin, copper, etc. The pressure-sensitive material may be received in the polymer resin in a form of particles. The disclosure is not limited thereto.

In case that a pressure is applied to the first pressure sensor 263, the first pressure sensor electrode 266, the pressure sensing layer 269, and the second pressure sensor electrode 267 may be electrically connected to each other. An electrical resistance of the pressure sensing layer 269 may be lowered due to the pressure applied to the first pressure sensor 263. A pressure driving voltage may be applied to the first pressure sensor electrode 266 and a pressure sensing voltage may be measured through the second pressure sensor electrode 267. Thus, an electrical resistance of the pressure sensing layer 269 may be calculated. Depending on the electrical resistance of the pressure sensing layer 269, whether or not the pressure is applied, and a magnitude of the pressure may be calculated.

The first pressure sensor electrodes 266 may extend in the fourth direction DR4 and may be arranged or disposed in the fifth direction DR5. The second pressure sensor electrodes 267 may extend in the fifth direction DR5 and may be arranged or disposed in the fourth direction DR4. The first pressure sensor electrodes 266 and the second pressure sensor electrodes 267 may intersect with each other. Intersection areas of the first pressure sensor electrodes 266 and the second pressure sensor electrodes 267 may be arranged or disposed in a matrix form. Each of the intersection areas of the first pressure sensor electrodes 266 and the second pressure sensor electrodes 267 may act as a pressure sensing cell for sensing a pressure. For example, the pressure may be sensed in each of the intersection areas of the first pressure sensor electrodes 266 and the second pressure sensor electrodes 267. In FIG. 12, an example in which the number of the first pressure sensor electrodes 266 is 8 and the number of the second pressure sensor electrodes 267 is 8 is illustrated for convenience of description. However, the numbers of the first and second pressure sensor electrodes 266 and 267 are not limited thereto.

In case that each of the first and second pressure sensor electrodes 266 and 267 may include a non-transparent conductive material, or the pressure sensing layer 269 may include a non-transparent polymer resin, the first pressure sensor 263 may be opaque. To prevent light from the first light-emitting member 262 from being blocked with the first pressure sensor 263, the first pressure sensor 263 may include the first optical hole LH1. A component including a non-transparent material among the first pressure sensor electrode 266, the second pressure sensor electrode 267, and the pressure sensing layer 269 may be removed from the first optical hole LH1. For example, in case that each of the first and second pressure sensor electrodes 266 and 267 may include a non-transparent conductive material, the first and second pressure sensor electrodes 266 and 267 may be removed from the first optical hole LH1. In case that the pressure sensing layer 269 may include a non-transparent polymer resin, the pressure sensing layer 269 may be removed from the first optical hole LH1. In case that the first and second pressure sensor electrodes 266 and 267 include a non-transparent conductive material and the pressure sensing layer 269 may include a non-transparent polymer resin, the first and second pressure sensor electrodes 266 and 267, and the pressure sensing layer 269 may be removed from the first optical hole LH1.

Figure 14:
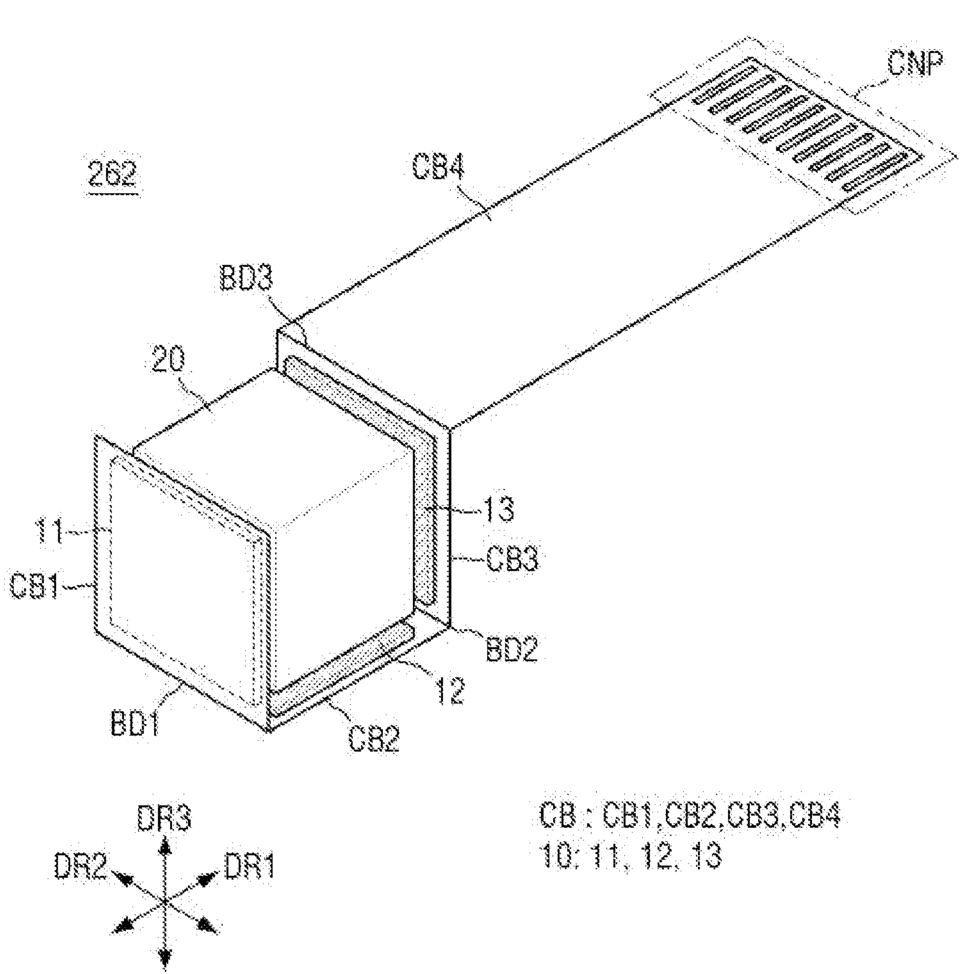
FIG. 14 is a schematic perspective view showing the light-emitting member shown in FIG. 11.
Figure 15:
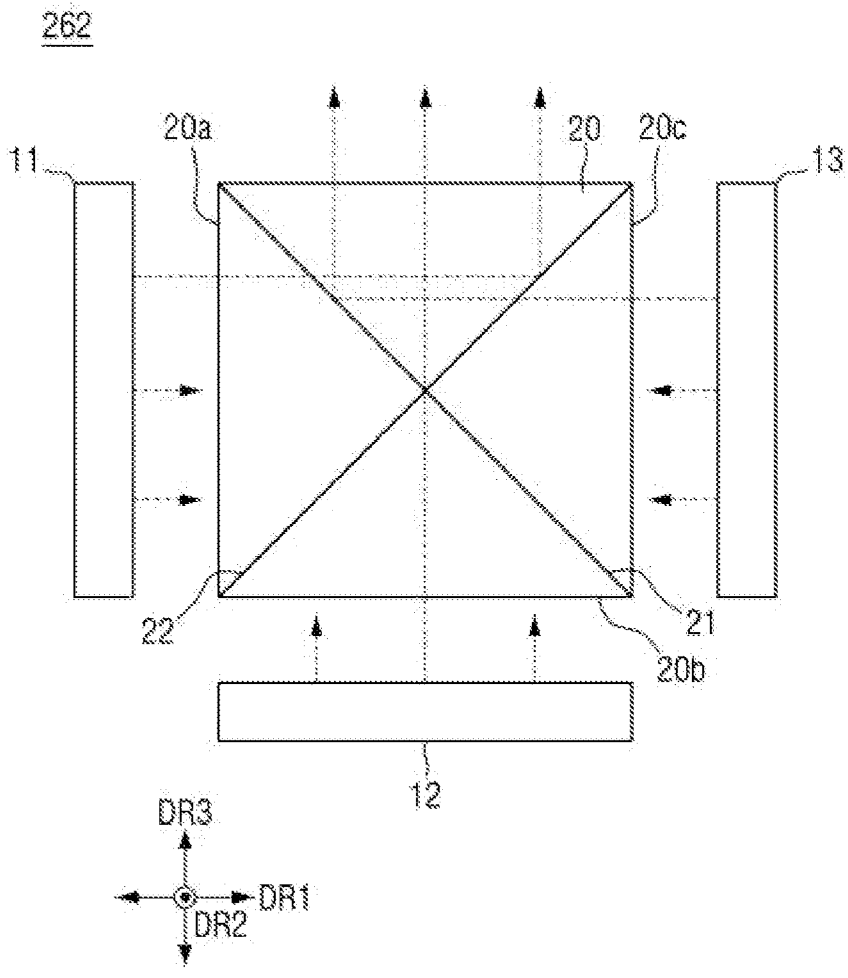
FIG. 15 is a side view showing the light-emitting member shown in FIG. 14 in more detail.

FIG. 14 is a schematic perspective view showing a light-emitting member shown in FIG. 11. FIG. 15 is a side view showing the light-emitting member shown in FIG. 14 in more detail. Although FIG. 14 and FIG. 15 show a detailed structure of the first light-emitting member 262, a configuration of the second light-emitting member 282 may also have the same structure as that of the first light-emitting member 262.

Referring to FIG. 14 and FIG. 15, the first light-emitting member 262 may include a light-emitting panel 10: 11, 12, and 13, a circuit board CB: CB1, CB2, CB3, and CB4, and an optical coupler 20.

The light-emitting panel 10: 11, 12, 13 may include a first light-emitting panel 11 that emits the first color light of the visible-light wavelength band, the second color light of the visible-light wavelength band, a second light-emitting panel 12 that emits the second color light of the visible-light wavelength band, and a third light-emitting panel 13 that emits the third color light of the infrared ray wavelength band.

Each of the first light-emitting panel 11, the second light-emitting panel 12, and the third light-emitting panel 13 may have a LEDoS (Light Emitting Diode on Silicon) structure in which light-emitting diode elements are disposed on a semiconductor circuit board formed using a semiconductor process. For example, the first light-emitting panel 11 may include an image display unit 110 that emits the first color light of the visible-light wavelength band. The second light-emitting panel 12 may include an image display unit 110 that emits the second color light of the visible-light wavelength band. Moreover, the third light-emitting panel 13 may include an image display unit 110 that emits the third color light of the infrared ray wavelength band.

Since a detailed layout structure of the image display unit 110 is the same as a layout structure of the image display unit 110 as described through FIG. 5 to FIG. 9, description of a detailed layout structure of each of the first to third light-emitting panels 11, 12, and 13 will be replaced with the description of the layout structure of the image display unit 110 as described through FIG. 5 to FIG. 9. However, each of pixels PX emitting the first color light of the visible-light wavelength band may be disposed in the image display unit 110 of the first light-emitting panel 11. Each of pixels PX emitting the second color light of the visible-light wavelength band may be disposed in the image display unit 110 of the second light-emitting panel 12. Each of pixels PX that emit the third color light of the infrared ray wavelength band may be disposed in the image display unit 110 of the third light-emitting panel 13.

The circuit board CB: CB1, CB2, CB3, and CB4 may be disposed on a rear face of the light-emitting panel 10: 11, 12, and 13. The circuit board CB: CB1, CB2, CB3, and CB4 may be attached to the rear face of the light-emitting panel 10: 11, 12, and 13 via one of an adhesive sheet, a liquid adhesive, a pressure-sensitive adhesive, and a double-sided tape. The disclosure is not limited thereto.

The circuit board CB: CB1, CB2, CB3, and CB4 may include a first circuit portion CB1, a second circuit portion CB2, a third circuit portion CB3, and a fourth circuit portion CB4, and may include a first connection portion BD1, a second connection portion BD2, and a third connection portion BD3 disposed therebetween.

The first light-emitting panel 11 may be disposed on the first circuit portion CB1. The first circuit portion CB1 may be adjacent to a first side face 20*a* of the optical coupler 20. Accordingly, the first circuit portion CB1, the first light-emitting panel 11, and the first side face 20*a* of the optical coupler 20 may be arranged or disposed along the first direction DR1.

The second light-emitting panel 12 may be disposed on the second circuit portion CB2. The second circuit portion CB2 may be adjacent to a second side face 20*b* of the optical coupler 20. Accordingly, the second circuit portion CB2, the second light-emitting panel 12, and the second side face 20*b* of the optical coupler 20 may be arranged or disposed along the third direction DR3.

The third light-emitting panel 13 may be disposed on the third circuit portion CB3. The third circuit portion CB3 may be adjacent to a third side face 20*c* of the optical coupler 20. Accordingly, the third circuit portion CB3, the third light-emitting panel 13, and the third side face 20*c* of the optical coupler 20 may be arranged or disposed along the first direction DR1.

The fourth circuit portion CB4 may act as an area connected to an external connector (not shown). The fourth circuit portion CB4 may include a connector connection portion CNP. The connector connection portion CNP may provide a space for electrically connecting the external connector and the conductive lines included in the circuit board CB to each other.

Each of the first to third connection portions BD1, BD2, and BD3 may refer to an area at which the circuit board is readily folded or bent in a plan view.

The first connection portion BD1 may be disposed between the first circuit portion CB1 and the second circuit portion CB2 to connect the first circuit portion CB1 and the second circuit portion CB2 to each other. In case that the circuit board is bent at the first connection portion BD1, the first light-emitting panel 11 disposed on the first circuit portion CB1 and the second light-emitting panel 12 disposed on the second circuit portion CB2 may face in different directions. For example, a top face of the first light-emitting panel 11 may face toward the first side face 20*a* of the optical coupler 20, and a top face of the second display panel 12 may face toward the second side face 20*b* of the optical coupler 20.

Since the circuit board may be bent at the first connection portion BD1 substantially at a right angle, the first light-emitting panel 11 and the second light-emitting panel 12 may extend in different directions perpendicular to each other.

The second connection portion BD2 may be disposed between the second circuit portion CB2 and the third circuit portion CB3 to connect the second circuit portion CB2 and the third circuit portion CB3 to each other. In case that the circuit board is bent at the second connection portion BD2, the second light-emitting panel 12 disposed on the second circuit portion CB2 and the third light-emitting panel 13 disposed on the third circuit portion CB3 may face in different directions. For example, as shown in FIG. 14, a top face of the third light-emitting panel 13 may face toward the third side face 20*c* of the optical coupler 20. The second light-emitting panel 12 and the third light-emitting panel 13 may extend in different directions perpendicular to each other.

The third connection portion BD3 may be disposed between the third circuit portion CB3 and the fourth circuit portion CB4, and the third connection portion BD3 may connect the third circuit portion CB3 and the fourth circuit portion CB4 to each t other.

The first circuit portion CB1, the second circuit portion CB2, the third circuit portion CB3, and the fourth circuit portion CB4 may be connected to each other via the first to third connection portions BD1, BD2, and BD3 to constitute one circuit board CB. The first circuit portion CB1, the second circuit portion CB2, the third circuit portion CB3, and the fourth circuit portion CB4 may be sequentially arranged or disposed along the first direction DR1.

The circuit board CB: CB1, CB2, CB3, and CB4 may be embodied as a flexible film such as a flexible printed circuit board (FPCB), a printed circuit board (PCB), flexible printed circuit (FPC) or a chip on film (COF).

The optical coupler 20 may be surrounded with the first circuit portion CB1, the second circuit portion CB2, and the third circuit portion CB3 of the circuit board CB and may be surrounded with the first light-emitting panel 11, the second light-emitting panel 12, and the third light-emitting panel 13 on the circuit board CB.

The optical coupler 20 may have a form of a rectangular parallelepiped or a cube, or the like in which four triangular prisms are combined with each other. The optical coupler 20 may include the first side area 20*a* facing toward the first light-emitting panel 11, the second side face 20*b* facing toward the second display panel 12, and the third side face 20*c* facing toward the third light-emitting panel 13.

The first side face 20*a* of the optical coupler 20 and the third side face 20*c* of the optical coupler 20 may extend in the third direction DR3 in a plan view, and may face toward each other. The first side face 20*a* of the optical coupler 20 and the third side face 20*c* of the optical coupler 20 may extend in a direction perpendicular to the extension direction of the second side face 20*b* of the optical coupler 20.

The optical coupler 20 may refer to an optical means for converging the first to third light from the first to third light-emitting panels 11, 12, and 13 into one direction or in a direction. The first light of the first light-emitting panel 11 may be incident perpendicularly onto the first side face 20*a* of the optical coupler 20. The second light of the second display panel 12 may be incident perpendicularly onto the second side face 20*b* of the optical coupler 20, and the third light of the third light-emitting panel 13 may be incident perpendicularly onto the third side face 20*c* of the optical coupler 20.

The optical coupler 20 may include a first reflective transmissive layer 21 and a second reflective transmissive layer 22. The first reflective transmissive layer 21 reflects the first color light in a wavelength band in a range of a preset first light reflection range, and transmits therethrough the second color and the third color light in a wavelength band in a range of a preset first light transmission range. On the contrary, the second reflective transmissive layer 22 may have a preset second light reflection range and a second light transmission range. The second reflective transmissive layer 22 may reflect the third color light of the wavelength band in a range of the second light reflection range, and transmit therethrough the light of the first color and the second color of a wavelength band in a range of the preset second light transmission range. In one example, the light of the first color incident on the first side face 20*a* of the optical coupler 20 may pass through the second reflective transmissive layer 22 and may be reflected from the first reflective transmissive layer 21. The third color light incident on the third side face 20*c* of the optical coupler 20 may pass through the first reflective transmissive layer 21 and may be reflected from the second reflective transmissive layer 22. Since the first reflective transmissive layer 21 and the second reflective transmissive layer 22 of the optical coupler 20 do not reflect the light of the second color therefrom, the light of the second color incident on the second side face 20*b* of the optical coupler 20 may pass therethrough.

The first detection processor 275 selects one of the first to third light-emission control signals and outputs the selected one to the first light-emission driver 272 to control the first light-emitting member 262 to emit light of one of the first color of the visible-light wavelength band, the second color of the visible-light wavelength band, or the third color of the infrared ray wavelength band. Moreover, the first light-emission driver 272 may selectively drive the first to third light-emitting panels 11, 12, and 13 based on the first to third light-emission control signals.

Figure 16:
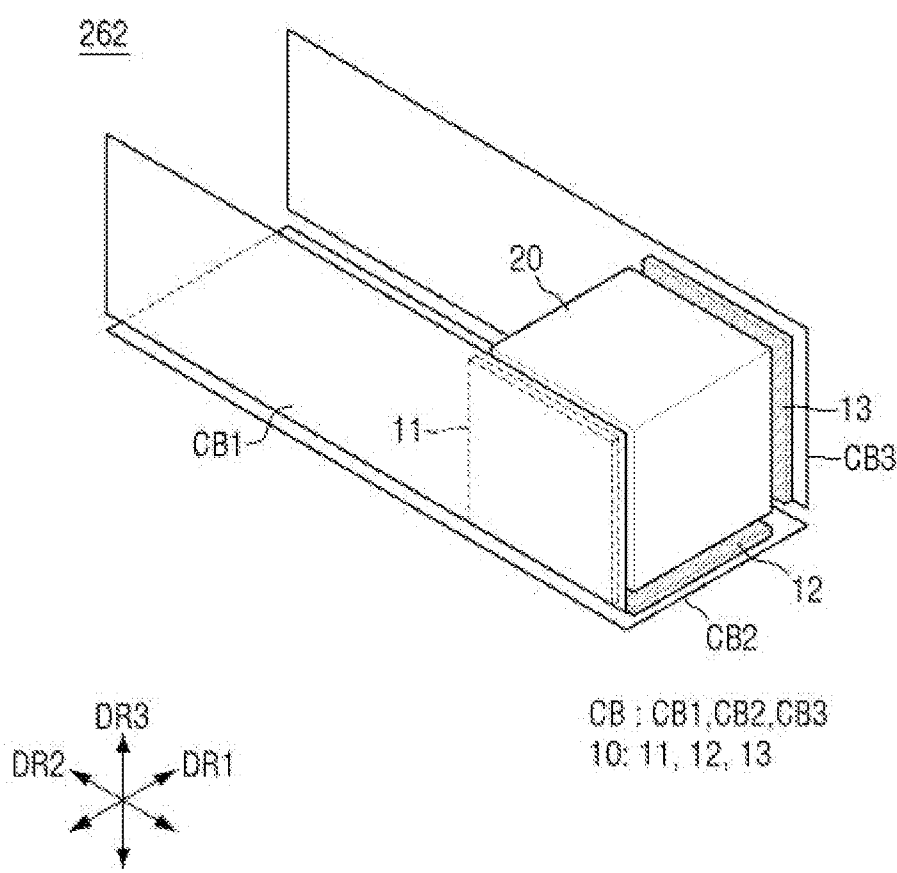
FIG. 16 is a schematic perspective view of an embodiment showing the light-emitting member shown in FIG. 11.
Figure 17:
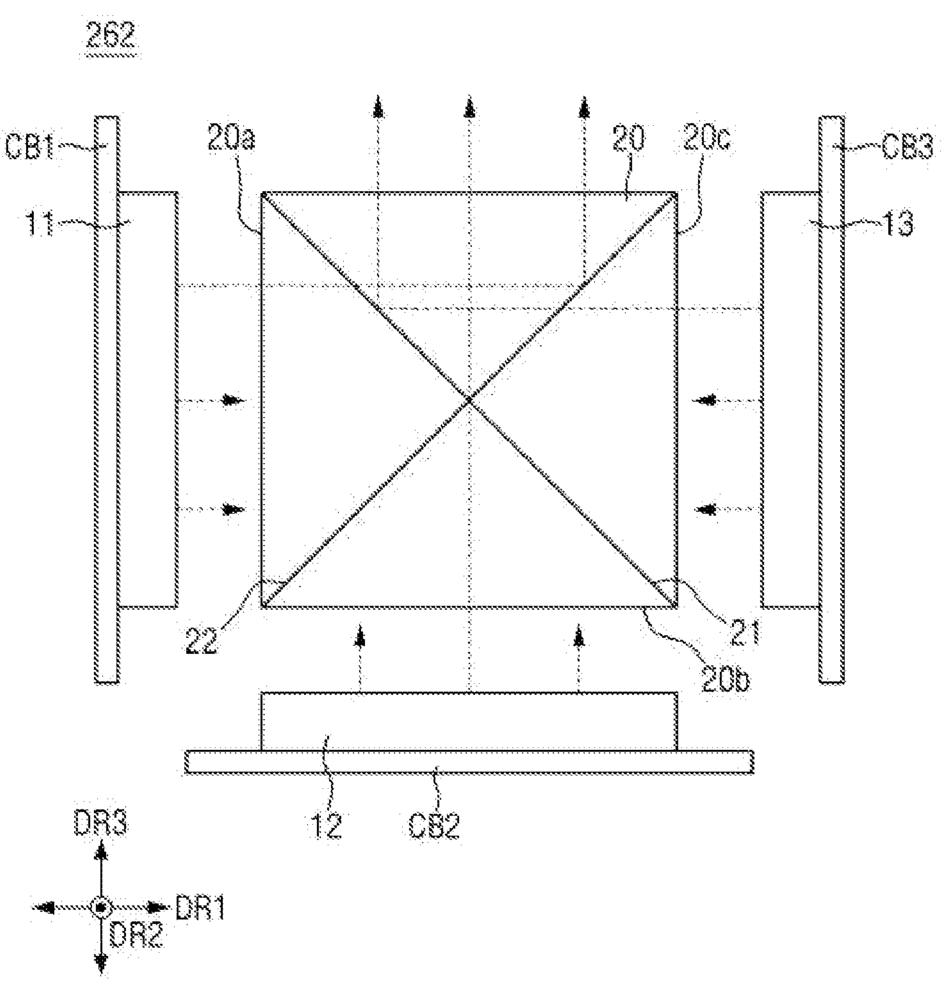
FIG. 17 is a side view showing the light-emitting member shown in FIG. 16 in more detail.

FIG. 16 is a schematic perspective view of an embodiment showing the light-emitting member shown in FIG. 11. Moreover, FIG. 17 is one side view or a side view showing the light-emitting member shown in FIG. 16 in more detail. FIGS. 16 and 17 also show a detailed structure of the first light-emitting member 262. However, a configuration of the second light-emitting member 282 may also have the same structure as that of the first light-emitting member 262.

Referring to FIG. 16 and FIG. 17, the first light-emitting member 262 may include light-emitting panels 10: 11, 12, and 13 respectively emitting light of different colors, a circuit board CB: CB1, CB2, CB3, and CB4 on which the light-emitting panels 10: 11, 12, and 13 are mounted, and an optical coupler 20.

The light-emitting panels 10: 11, 12, and 13 may include a first light-emitting panel 11 which emits green color light in the visible-light wavelength band, a second light-emitting panel 12 which emits blue color light in the visible-light wavelength band, and a third light-emitting panel 13 that emits red color light in the visible-light wavelength band.

Each of the first to third light-emitting panels 10: 11, 12, and 13 may have a LEDoS (Light Emitting Diode on Silicon) structure in which light-emitting diode elements are disposed on a semiconductor circuit board formed by a semiconductor process. In one example, the first light-emitting panel 11 may include an image display unit 110 that emits green color light of the visible-light wavelength band. The second light-emitting panel 12 may include an image display unit 110 that emits blue color light of the visible-light wavelength band. Moreover, the third light-emitting panel 13 may include an image display unit 110 that emits red color light of the visible-light wavelength band. Accordingly, each of the pixels PX emitting green color light of the visible-light wavelength band may be disposed in the image display unit 110 of the first light-emitting panel 11. Each of the pixels PX emitting blue color light of the visible-light wavelength band may be disposed in the image display unit 110 of the second light-emitting panel 12. Each of the pixels PX emitting red color light of the visible-light wavelength band may be disposed in the image display unit 110 of the third light-emitting panel 13.

Since the detailed layout structure of the image display unit 110 disposed in each of the light-emitting panels 10: 11, 12, and 13 is the same as the layout structure of the image display unit 110 as described through FIG. 5 to FIG. 9, description of the detailed layout structure of each of the first to third light-emitting panels 11, 12, and 13 will be replaced with description of the layout structure of the image display unit 110 as described through FIG. 5 to FIG. 9.

Each of the light-emitting panels 10: 11, 12, and 13 may be mounted on one face or a face of each of the circuit portions CB1, CB2, CB3, and CB4 of the circuit board CB. Each of the circuit portions CB1, CB2, CB3, and CB4 of the circuit board CB may be attached to a rear face of each of the light-emitting panels 10: 11, 12, and 13 via one of an adhesive sheet, a liquid adhesive, a pressure-sensitive adhesive, and a double-sided tape. However, the disclosure is not limited thereto. The circuit board CB: CB1, CB2, CB3, and CB4 may include a first circuit portion CB1, a second circuit portion CB2, a third circuit portion CB3, and a fourth circuit portion CB4.

Each of the first circuit portion CB1, the second circuit portion CB2, the third circuit portion CB3, and the fourth circuit portion CB4 may constitute a separate circuit board CB. Each of these circuit boards CB: CB1, CB2, CB3, and CB4 may be embodied as a flexible film such as a flexible printed circuit board (FPCB), a printed circuit board (PCB), flexible printed circuit (FPC) or a chip on film (COF).

The optical coupler 20 may have a form of a rectangular parallelepiped, a cube, or the like in which four triangular prisms are combined to each other. The optical coupler 20 may include a first side face 20*a* facing toward the first light-emitting panel 11, a second side face 20*b* facing toward the second display panel 12, and a third side facing 20*c* toward the third light-emitting panel 13. The optical coupler 20 may refer to optical means for converging the first to third light from the first to third light-emitting panels 11, 12, and 13 into one direction or in a direction. The first light of the first light-emitting panel 11 may be incident perpendicularly onto the first side face 20*a* of the optical coupler 20. The second light of the second display panel 12 may be incident perpendicularly onto the second side face 20*b* of the optical coupler 20. The third light of the third light-emitting panel 13 may be incident perpendicularly onto the third side face 20*c* of the optical coupler 20.

The first detection processor 275 generates the first to third light-emission control signals such that the first light-emitting panel 11 emits green light in the visible-light wavelength band, the second display panel 12 emits blue light in the visible-light wavelength band, and the third light-emitting panel 13 emits red light in the visible-light wavelength band. Moreover, the first detection processor 275 may output the first to third light-emission control signals to the first light-emission driver 272. Accordingly, the first light-emission driver 272 may selectively drive the first to third light-emitting panels 11, 12, and 13 based on the first to third light-emission control signals.

Figure 18:
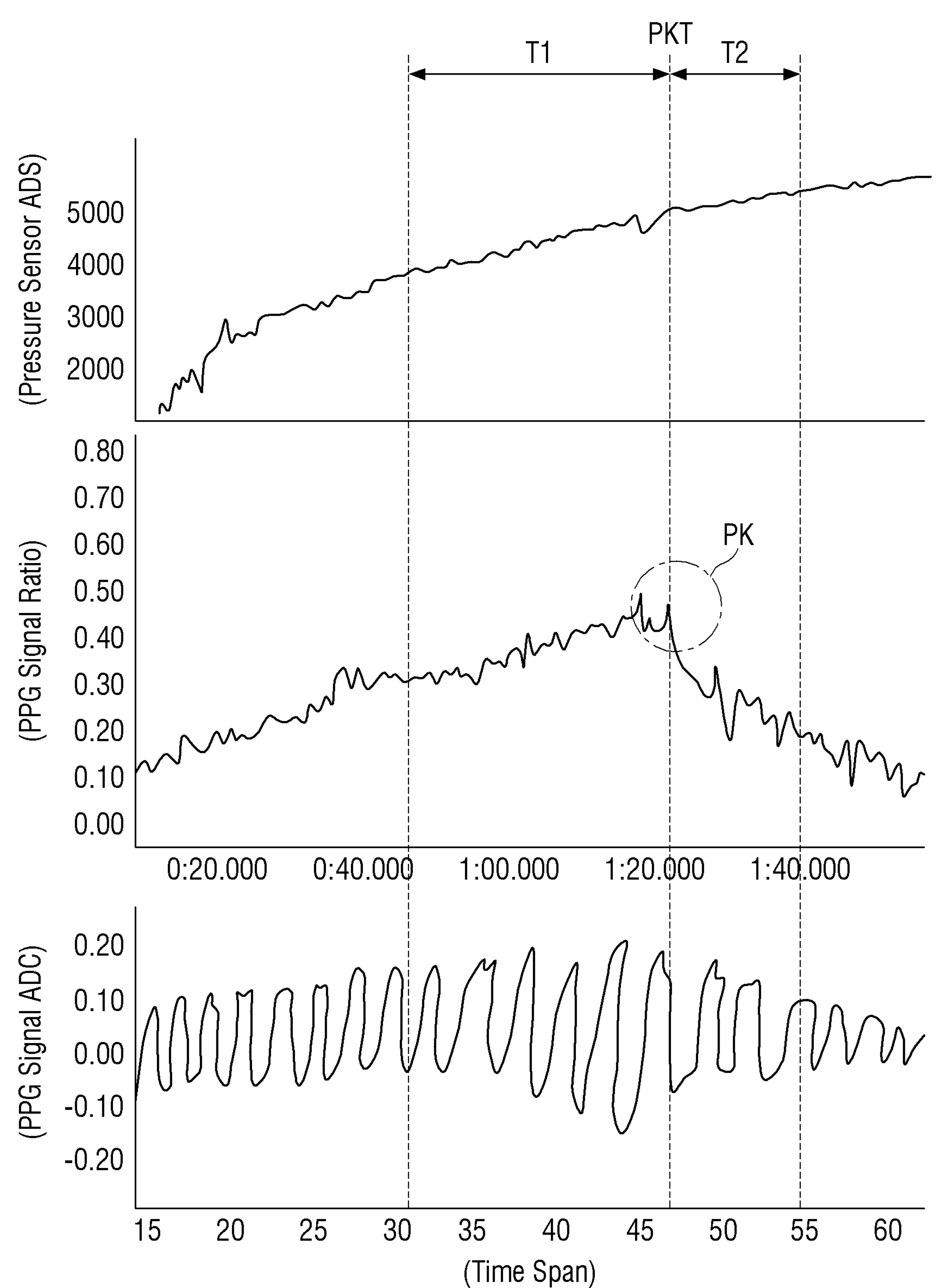
FIG. 18 is a graph for illustrating a blood-pressure information calculation method of a first detection processor shown in FIG. 10.

FIG. 18 is a graph for illustrating a blood-pressure related information calculation method of the first signal processing processor shown in FIG. 10.

Referring to FIG. 18, the first detection processor 275 may generate a pulse wave signal based on the pressure applied from the user, based on a pressure value (a pressure sensor ADC) calculated by the first pressure sensor 263 and an optical signal (PPG Signal Ratio) based on the light amount detected by the first light-receiving sensor 265, and may calculate a blood-pressure based on the pulse wave signal. The pulse wave signal may have a waveform in which a wave vibrates according to a heartbeat cycle. For example, the first detection processor 275 may estimate respectively blood-pressures of blood vessels of the user's skin OBJ, based on time differences between time points corresponding to peaks PK of the calculated pulse wave signal and time points corresponding to peaks of a filtered pulse wave.

The first detection processor 275 may calculate pulse wave signals for preset periods T1 and T2 before and after each of the time points PKT corresponding to the peak PKs of the calculated pulse wave signal and may detect the blood-pressures based on differences between the pulse wave signals. A blood-pressure having a maximum value among the estimated blood-pressures may be calculated as a systolic blood-pressure, and a blood-pressure having a minimum value among the estimated blood-pressures may be calculated as a diastolic blood-pressure. Further, an average blood-pressure, a heart rate, and blood flow change may be calculated using the estimated blood-pressures.

A method for measurement of the blood-pressure, the heart rate, and the oxygen saturation is only an example. Various other methods are disclosed in Korean Patent Application Publication No. 10-2018-0076050, Korean Patent Application Publication No. 10-2017-0049280, Korean Patent Application Publication No. 10-2019-0040527, etc. Contents disclosed in the above patent publication documents may be incorporated herein as fully disclosed in the disclosure.

Figure 19:
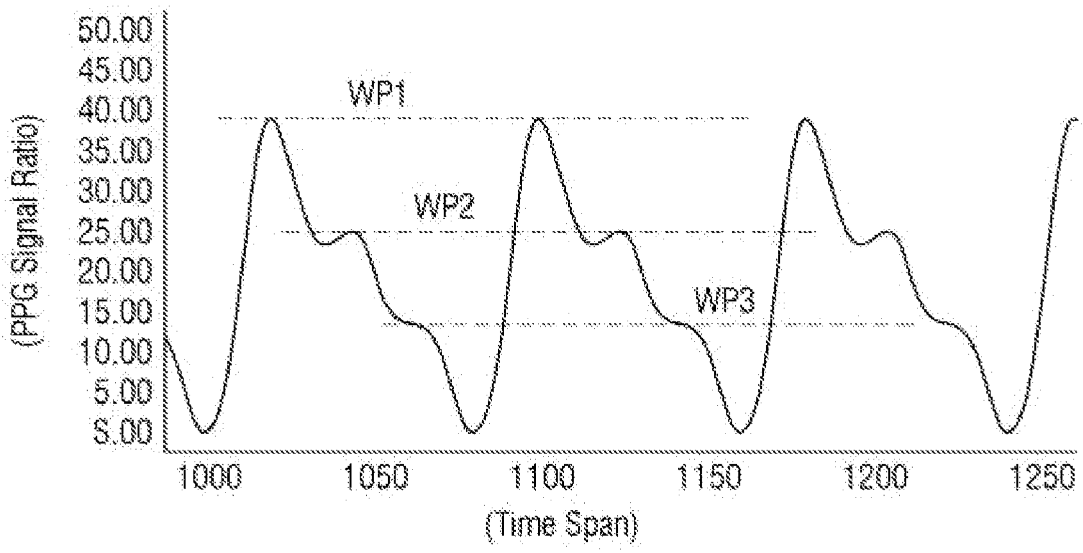
FIG. 19 is a graph for illustrating a blood-pressure information calculation method of the first detection processor based on change in a light-emitting color of the first light-emitting member shown in FIG. 10.

FIG. 19 is a graph for illustrating a blood-pressure related information calculation method of a first signal processing processor, based on change in a light-emitting color of the first light-emitting member shown in FIG. 10.

Referring to FIG. 19 (and FIG. 10), the first detection processor 275 may sequentially select one light-emission control signal from among from the first to third light-emission control signals and output the selected one to the first light-emission driver 272. The first light-emission driver 272 may sequentially drive the first to third light-emitting panels 11, 12, and 13 based on the first to third light-emission control signals that are sequentially input thereto. The first light-emitting member 262 may sequentially generate and emit the first color of the visible-light wavelength band, the second color of the visible-light wavelength band, or the third color of the infrared ray wavelength band.

The first detection processor 275 may sequentially identify a peak value detection period WP1 according to emission of the red color light of the infrared ray wavelength band from an optical signal received through the first light-receiving sensor 265, a first continuous waveform detection period WP2 according to emission of green color light of the visible-light wavelength band, and a second continuous waveform detection period WP3 according to emission of the infrared ray light and may analyze the optical signal for the sequentially identified periods. Accordingly, a main processor may accurately detect a peak value of the waveform detected during the blood-pressure measurement, and a waveform that is continuously detected, and detect the blood-pressure, the heart rate, and the oxygen saturation for the sequentially identified periods.

Figure 20:
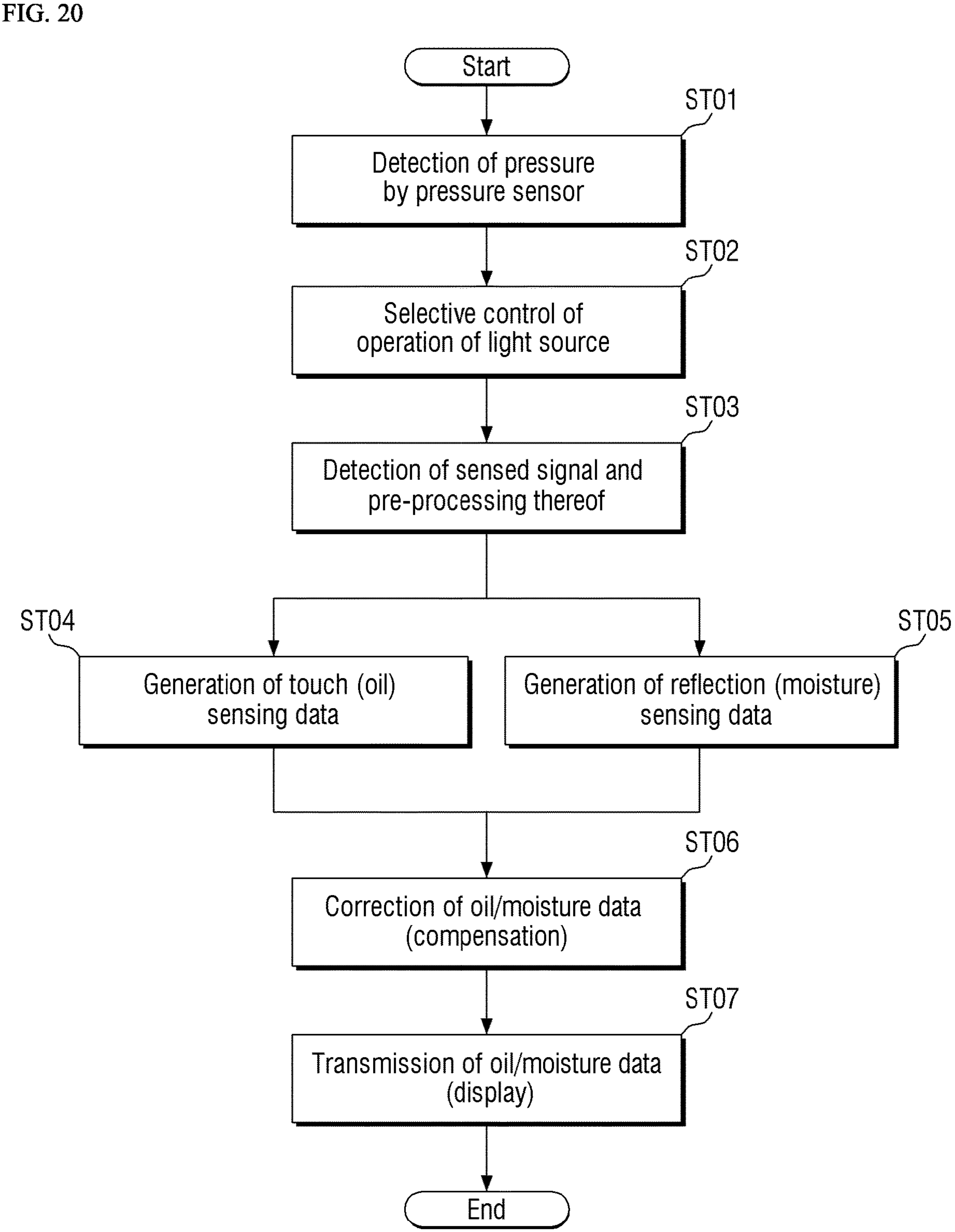
FIG. 20 is a flowchart for illustrating a skin related information detection method of a second detection processor shown in FIG. 10.

FIG. 20 is a flowchart for illustrating a skin related information detection method of a second signal processing processor shown in FIG. 10. Moreover, FIG. 21 is a graph for illustrating a skin oil level and moisture level calculation method of the first signal processing processor shown in 10.

Figure 21:
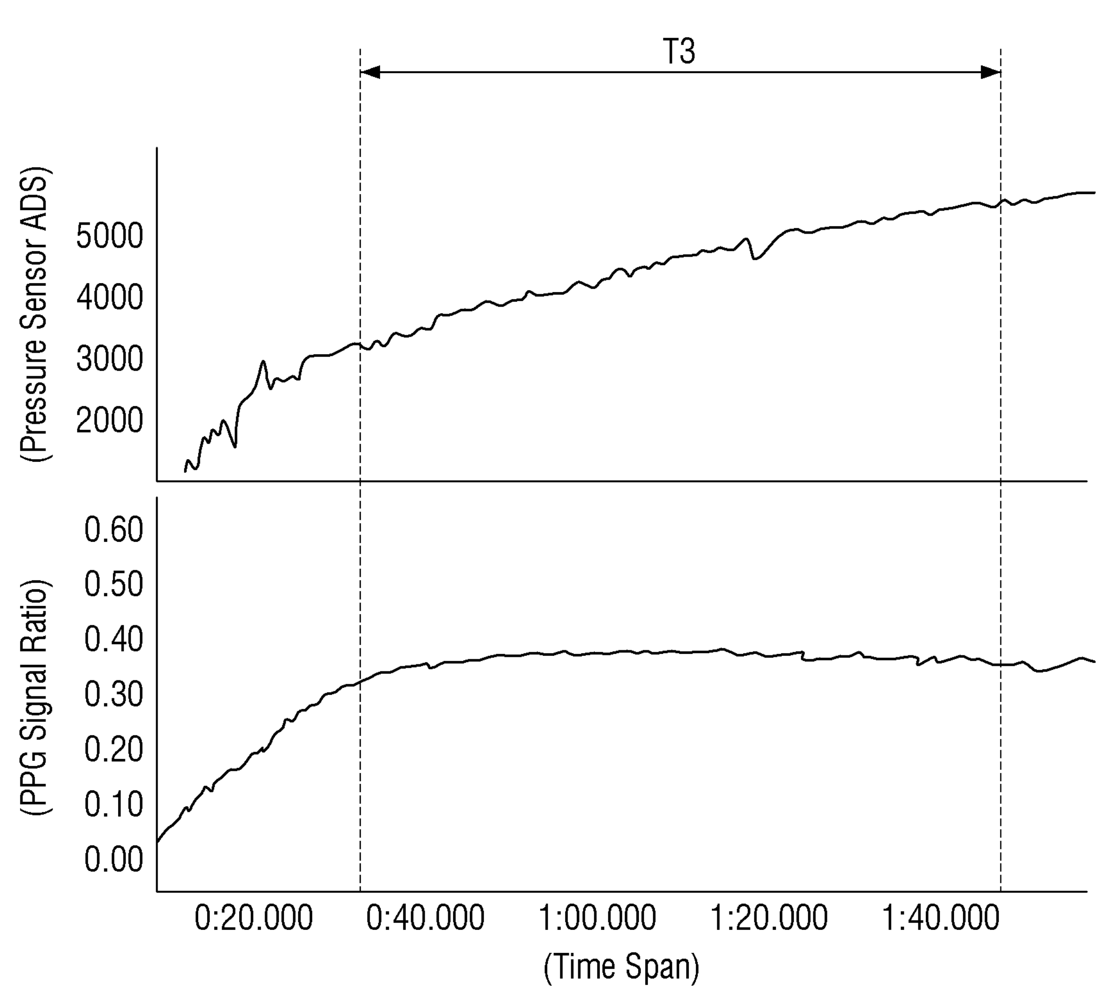
FIG. 21 is a graph for illustrating a skin oil level and moisture level calculation method of the second detection processor shown in FIG. 10.

Referring to FIG. 20 and FIG. 21, in case that the pressure data is input from the second converter 293 to the second detection processor 295, the second detection processor 295 calculates a pressure value applied to the second pressure sensor 283 to recognize the pressure toward the user's skin in ST01.

In case that a pressure is applied to the second pressure sensor 283, the second detection processor 295 selects one of the first to third light-emission control signals and outputs the selected one to the second light-emission driver 292 to control the second light-emitting member 282 to emit light of one of the first color or the second color of the visible-light wavelength band, or the third color of the infrared ray wavelength band in ST02.

The second signal processor 291 filters and rectifies the optical signal received from the second light-receiving sensor 285. Moreover, the second signal processor 291 may sample the filtered and rectified optical signal and convert the sampled signal into a digital signal, and transmit the digital signal to the second detection processor 295 in ST03.

Referring to FIG. 21, an optical signal received from the second light-receiving sensor 285 corresponds to an amount of reflected light varying depending on the skin moisture level and the oil level. Accordingly, the amount of the reflected light may vary in proportion to the skin moisture level and oil level.

The second detection processor 295 sequentially writes, into a memory, digital signals into which the second signal processor 291 converts the optical signals for a preset touch detection period T3 of a period for which a pressure is applied to the second pressure sensor 283, and generates reflected amount sensing data based on the digital signals in ST03. Moreover, the second detection processor 295 may compare the reflected amount sensing data for the touch detection period T3 with preset moisture comparison data and generate moisture level detection data based on the comparison result in ST05.

In one example, in case that the current amount varies due to the contact of the capacitance sensor 286 with the user's skin or the object, the capacitance sensor 286 transmits the varied current amount to the second converter 293 or the second detection processor 295. Accordingly, the second detection processor 295 generates a current amount change signal or data based on the current amount of an electrical signal input from the capacitance sensor 286. Moreover, the second detection processor 295 may compare the current amount change data with preset oil comparison data, and generate oil level detection data based on the comparison result in ST04.

The second detection processor 295 corrects the oil level detection data and the moisture level detection data to be adapted to a preset augmented reality content image data format in ST06, and transmits the corrected oil level detection data and the corrected moisture level detection data to the control module 220. Accordingly, the control module 220 may control the image display module 210 to display the contents including the oil level detection data and the moisture level detection data as augmented reality content information in ST07.

In concluding the detailed description, those skilled in the art will appreciate that many variations and modifications can be made to the embodiments without substantially departing from the principles of the disclosure. Therefore, the disclosed embodiments are used in a generic and descriptive sense only and not for purposes of limitation.

What is claimed is:

1. A device for providing augmented reality, the device comprising:

a support frame supporting at least one transparent lens comprising a left lens and a right lens;

an image display module that generates, transmits and displays augmented reality content through the at least one transparent lens, wherein the image display module does not overlap a center of the left lens or a center of the right lens;

a blood-pressure information detector connected to the support frame that detects at least one blood-pressure related information including a blood-pressure, a heart rate, and oxygen saturation of a user in case that a skin of the user touches the blood-pressure information detector;

a skin information detector connected to the support frame that detects at least one skin related information including a moisture level and an oil level of the user's skin in case that the user's skin touches the skin information detector, the skin information detector comprising an optical pair including a light-emitting member and a light-receiving sensor configured to measure skin moisture level, and a capacitance sensor configured to detect a current variation under skin contact, the current variation being processed to obtain the skin oil level, wherein the skin information detector further comprises:

a second housing having an inner groove, and a second light-emitting member seated in the inner groove and facing in a frontward direction from the second housing;

a second pressure sensor facing in the frontward direction from the second housing and disposed on and overlapping a front face of the second light-emitting member in a plan view;

a second substrate fixed on a front face of the second pressure sensor, the second light-receiving sensor being fixed to the second substrate and disposed on and overlapping a front partial area of the second pressure sensor in the plan view, and facing in the frontward direction from the second pressure sensor;

the capacitance sensor fixed to the second substrate, disposed on and overlapping a front partial area of the second pressure sensor in the plan view, and facing in the frontward direction from the second pressure sensor; and a second optical hole formed through each of the second pressure sensor and the second substrate corresponding to a light-emitting face of the second light-emitting member; and a control module that controls the image display module to display the at least one blood-pressure related and the at least one skin related information as augmented reality contents.

2. The device of claim 1, wherein the blood-pressure information detector includes:

a first light-emitting member that selectively emits one of a first color light of a visible-light wavelength band, a second color light of a visible-light wavelength band, and a third color light of an infrared ray wavelength band;

a first light-receiving sensor that detects light emitting from the first light-emitting member and reflected from the user's skin, and that outputs an optical signal corresponding to an amount of the reflected light;

a first pressure sensor that senses contact with the user's skin; and a first detection processor that:

in case that the user's skin contact with the first pressure sensor is sensed, calculates a pulse wave signal reflecting blood change according to heartbeat, based on the optical signal; and detects the blood-pressure related information based on the pulse wave signal.

3. The device of claim 2, wherein the blood-pressure information detector includes:

a first light-emission driver that transmits one of first to third drive signals to the first light-emitting member to control light-emission of the first light-emitting member in response to reception of one of first to third light-emission control signals input from the first detection processor;

a first signal processor that filters and rectifies the optical signal received from the first light-receiving sensor, and outputs the filtered and rectified signal as an analog signal to the first detection processor, or converts the analog signal into a digital signal by a sampling process and outputs the digital signal to the first detection processor; and a first converter that performs digital signal processing on an electrical pressure detection signal from the first pressure sensor to convert the electrical pressure detection signal to pressure data, and transmits the pressure data to the first detection processor.

4. The device of claim 2, wherein the first pressure sensor, the first light-emitting member and the first light-receiving sensor face in a frontward direction, and the first pressure sensor is disposed around and adjacent to the first light-emitting member and the first light-receiving sensor, or the first pressure sensor, the first light-emitting member and the first light-receiving sensor face in a frontward direction, and the first pressure sensor is disposed on and overlaps a front face of each of the first light-emitting member and the first light-receiving sensor in a plan view.

5. The device of claim 2, wherein the first light-emitting member faces in a frontward direction from a first housing and is disposed in an inner groove of the first housing, the first pressure sensor faces in the frontward direction from a first housing and is disposed on and overlaps a front face of the first light-emitting member in a plan view, the first light-receiving sensor is fixed to a first substrate and faces in a frontward direction from the first pressure sensor, and is disposed on and overlaps a front partial area of the first pressure sensor in a plan view, and the first pressure sensor and the first substrate each include a first optical hole corresponding to a light-emitting face of the first light-emitting member.

6. The device of claim 2, wherein the first pressure sensor includes:

a first base substrate and a second base substrate facing toward each other;

a first pressure sensor electrode disposed on the first base substrate;

a second pressure sensor electrode disposed on the second base substrate; and a pressure sensing layer overlapping the first pressure sensor electrode and the second pressure sensor electrode in a plan view.

7. The device of claim 6, wherein the first pressure sensor electrode and the second pressure sensor electrode each include a transparent conductive material, and the pressure sensing layer includes a transparent polymer resin.

8. A device for providing augmented reality, the device comprising:

a support frame supporting at least one transparent lens comprising a left lens and a right lens;

an image display module that generates, transmits and displays augmented reality content through the at least one transparent lens, wherein the image display module does not overlap a center of the left lens or a center of the right lens;

a blood-pressure information detector connected to the support frame that detects at least one blood-pressure related information including a blood-pressure, a heart rate, and oxygen saturation of a user in case that a skin of the user touches the blood-pressure information detector, the blood-pressure information detector including:

a first light-emitting member that selectively emits one of a first color light of a visible-light wavelength band, a second color light of a visible-light wavelength band, and a third color light of an infrared ray wavelength band;

a first light-receiving sensor that detects light emitting from the first light-emitting member and reflected from the user's skin, and that outputs an optical signal corresponding to an amount of the reflected light;

a first pressure sensor that senses contact with the user's skin; and a first detection processor that, in case that the user's skin contact with the first pressure sensor is sensed, calculates a pulse wave signal reflecting blood change according to heartbeat based on the optical signal, detects the blood-pressure related information based on the pulse wave signal; and a control module that controls the image display module to display the at least one blood-pressure related information as augmented reality contents, wherein the first light-emitting member includes:

a circuit board including a first circuit portion, a second circuit portion, and a third circuit portion;

a first light-emitting panel disposed on the first circuit portion that emits the first color light;

a second light-emitting panel disposed on the second circuit portion that emits the second color light;

a third light-emitting panel disposed on the third circuit portion that emits the third color light; and an optical coupler that outputs at least one of the first color light from the first light-emitting panel, the second color light from the second light-emitting panel, and the third color light from the third light-emitting panel.

9. The device of claim 8, wherein the first light-emitting panel includes an image display unit that emits the first color light, the second light-emitting panel includes an image display unit that emits the second color light, and the third light-emitting panel includes an image display unit that emits the third color light, and the image display unit included in each of the first light-emitting panel, the second light-emitting panel and the third light-emitting panel includes:

a partitioning wall disposed on a substrate and patterned in a matrix;

light-emitting elements respectively disposed in light-emitting areas partitioned from each other by the partitioning wall and disposed in the matrix, wherein light-emitting elements each extend in a plan view of the substrate;

a base resin disposed in the light-emitting areas that receives the light-emitting elements; and optical patterns disposed in at least one of the light-emitting areas.

10. The device of claim 8, wherein the circuit board includes:

a first connection portion disposed between the first circuit portion and the second circuit portion; and a second connection portion disposed between the second circuit portion and the third circuit portion, and the circuit board is bent at each of the first connection portion and the second connection portion.

11. The device of claim 10, wherein the optical coupler includes:

a first reflective transmissive layer reflecting the first color light from the first light-emitting panel and transmitting the second color light and the third color light; and a second reflective transmissive layer reflecting the third light from the third light-emitting panel and transmitting the first color light and the second color light.

12. A device for providing augmented reality, the device comprising:

a support frame supporting at least one transparent lens;

an image display module that displays augmented reality content through the at least one transparent lens;

a blood-pressure information detector connected to the support frame that detects at least one blood-pressure related information including a blood-pressure, a heart rate, and oxygen saturation of a user in case that a skin of the user touches the blood-pressure information detector;

a skin information detector connected to the support frame that detects at least one skin related information including a moisture level and an oil level of the user's skin in case that the user's skin touches the skin information detector; and a control module that controls the image display module to display the at least one blood-pressure related and the at least one skin related information as augmented reality contents, wherein the skin information detector includes:

a second light-emitting member that emits one of a first color light of a visible-light wavelength band, a second color light of a visible-light wavelength band, and a third color light of an infrared ray wavelength band;

a second light-receiving sensor that detects light emitting from the second light-emitting member and reflected from the user's skin, and outputs an optical signal corresponding to an amount of the reflected light;

a capacitance sensor that outputs an electrical signal based on current varied in case that a reference current amount thereof varies due to the user's skin contact;

a second pressure sensor sensing the user's skin touch; and a second detection processor that:

in case that the user's skin touch with the second pressure sensor is sensed, the second detection processor detects a moisture level of the user's skin based on the optical signal and detects an oil level of the user's skin based on to the electrical signal based on the varied current; and detects the skin related information including the moisture level and the oil level.

13. The device of claim 3, wherein the second light-emitting member includes:

a circuit board including a first circuit portion, a second circuit portion, and a third circuit portion;

a first light-emitting panel disposed on the first circuit portion that emits the first color light;

a second light-emitting panel disposed on the second circuit portion that emits the second color light;

a third light-emitting panel disposed on the third circuit portion that emits the third color light; and an optical coupler that outputs at least one of the first color light from the first light-emitting panel, the second color light from the second light-emitting panel, and the third color light from the third light-emitting panel.

14. The device of claim 2, wherein the image display module includes:

an image display unit connected to a side or each of opposing sides of the support frame or integral with the support frame to display an image of augmented reality content; and an image transmission member that transmits the image to the transparent lens, and the image display module displays the image of the augmented reality content through the image transmission member and reflective members of the transparent lens by the control module.

15. The device of claim 14, wherein the image display unit includes:

a partitioning wall disposed on a substrate and patterned in a matrix;

light-emitting elements respectively disposed in light-emitting areas partitioned from each other by the partitioning wall and disposed in the matrix wherein the light-emitting elements each extend in the plan view of the substrate;

a base resin disposed in the light-emitting areas that receives the light-emitting elements; and optical patterns disposed in at least one of the light-emitting areas.

16. The device of claim 15, wherein the light-emitting areas include:

a first light-emitting area, a second light-emitting area, and a third light-emitting area, or a first light-emitting area, a second light-emitting area, a third light-emitting area, and a fourth light-emitting area disposed in each pixel area and disposed in the matrix.

17. The device of claim 16, wherein the first light-emitting area includes a first light-emitting element that emits light of a first color selected from red, green, and blue;

the second light-emitting area includes a second light-emitting element that emits light of a second color selected from red, green, and blue and different from the first color;

the third light-emitting area includes a third light-emitting element that emits light of a third color selected from red, green, and blue and different from the first and second colors; and the fourth light-emitting area includes a fourth light-emitting element that emits light of a fourth color, the light of the fourth color and one of the first color light, the second color light and the third color light being of a same wavelength band.

18. The device of claim 17, wherein the first light-emitting area, the second light-emitting area, the third light-emitting area and the fourth light-emitting area have a same size or a same planar area, and a distance between the first light-emitting area and the second light-emitting area neighboring each other in a horizontal direction or a diagonal direction, a distance between the second light-emitting area and the third light-emitting area neighboring each other in the horizontal direction or the diagonal direction, a distance between the first light-emitting area and the third light-emitting area neighboring each other in the horizontal direction or the diagonal direction, and a distance between the third light-emitting area and the fourth light-emitting area neighboring each other in the horizontal direction or the diagonal direction are equal to each other based on a size or a planar area of each of the first light-emitting area, the second light-emitting area, the third light-emitting area and the fourth light-emitting area.

19. The device of claim 17, wherein at least one of the sizes or at least one of planar areas of the first light-emitting area, the second light-emitting area, the third light-emitting area and the fourth light-emitting area are different from each other, and a distance between the first light-emitting area and the second light-emitting area neighboring each other in a horizontal direction or a diagonal direction, a distance between the second light-emitting area and the third light-emitting area neighboring each other in the horizontal direction or the diagonal direction, a distance between the first light-emitting area and the third light-emitting area neighboring each other in the horizontal direction or the diagonal direction, and a distance between the third light-emitting area and the fourth light-emitting area neighboring each other in the horizontal direction or the diagonal direction are equal to or different from each other based on a size or a planar area of each of the first light-emitting area, the second light-emitting area, the third light-emitting area and the fourth light-emitting area.

20. The device of claim 1, wherein the image display module is disposed on an outer side of the support frame facing away from the user.

* * * * *